(12) United States Patent
Dallmier et al.

(10) Patent No.: US 9,125,357 B2
(45) Date of Patent: Sep. 8, 2015

(54) METHODS FOR THE COMMERCIAL PRODUCTION OF TRANSGENIC PLANTS

(75) Inventors: Kenneth A. Dallmier, Mahomet, IL (US); Rene Quadt, Chapel Hill, NC (US); Aron Louis Silverstone, Durham, NC (US)

(73) Assignee: Syngenta Participations AG, Basel (CH)

( * ) Notice: Subject to any disclaimer, the term of this patent is extended or adjusted under 35 U.S.C. 154(b) by 1348 days.

(21) Appl. No.: 12/130,829

(22) Filed: May 30, 2008

(65) Prior Publication Data

US 2008/0319927 A1 Dec. 25, 2008

Related U.S. Application Data

(60) Provisional application No. 60/941,466, filed on Jun. 1, 2007.

(51) Int. Cl.
| | | |
|---|---|---|
| *A01H 1/00* | (2006.01) | |
| *A01H 5/10* | (2006.01) | |
| *C12N 15/82* | (2006.01) | |
| *G06Q 30/02* | (2012.01) | |
| *C07K 14/415* | (2006.01) | |
| *C12N 15/00* | (2006.01) | |

(52) U.S. Cl.
CPC .............. *A01H 5/10* (2013.01); *C12N 15/8242* (2013.01); *C12N 15/8245* (2013.01); *C12N 15/8257* (2013.01); *G06Q 30/0283* (2013.01)

(58) Field of Classification Search
USPC .................. 435/183; 536/23.2; 800/295, 298; 530/370
See application file for complete search history.

(56) References Cited

U.S. PATENT DOCUMENTS

| | | | |
|---|---|---|---|
| 5,675,065 A * | 10/1997 | Bergquist | ...................... 800/271 |
| 6,418,867 B1 * | 7/2002 | Erickson | ........................ 111/200 |
| 6,580,020 B1 * | 6/2003 | Marshall et al. | ........... 800/320.1 |
| 6,865,556 B2 | 3/2005 | Penner et al. | |
| 2003/0056243 A1 | 3/2003 | Penner et al. | |
| 2003/0135885 A1 * | 7/2003 | Lanahan et al. | .............. 800/284 |
| 2004/0040055 A1 | 2/2004 | Clair et al. | |
| 2004/0040060 A1 | 2/2004 | Clair | |
| 2004/0237143 A1 | 11/2004 | Stamp et al. | |
| 2004/0244074 A1 | 12/2004 | Jones et al. | |

FOREIGN PATENT DOCUMENTS

| | | |
|---|---|---|
| WO | WO 2005/000352 A1 | 1/2005 |
| WO | WO 2005/094340 A2 | 10/2005 |

OTHER PUBLICATIONS

Agegnehu, G., et al., "Yield Performance and Land-use Efficiency of Barley and Faba Bean Mixed Cropping in Ethiopian Highlands," *Europ. J. Agronomy*, Oct. 1, 2006, pp. 202-207, vol. 25, No. 3.
Bischoff, A., et al., "Seed Provenance Matters—Effects on Germination of Four Plant Species Used for Ecological Restoration," *Basic and Applied Ecology*, Jul. 3, 2006, pp. 347-359, vol. 7, No. 4.
Isselin-Nondedeu, F., et al., "Contributions of Vegetation Cover and Cattle Hoof Prints Towards Seed Runoff Control on Ski Pistes," *Ecological Engineering*, Oct. 2, 2006, pp. 193-201, vol. 27, No. 3.
Mc Cullum, C., et al., Application of Modern Biotechnology to Food and Agriculture: Food Systems Perspective, *J. Nutr Educ Behav.*, Nov. 1, 2003, pp. 319-332, vol. 35, No. 6.
Radford, I.J., et al., Nutrient Stress and Performance of Invasive *Hieracium lepidulum* and Co-occuring Species in New Zealand, *Basic and Applied Ecology*, Jul. 3, 2006, pp. 320-333, vol. 7.

\* cited by examiner

*Primary Examiner* — Phuong Bui

(74) *Attorney, Agent, or Firm* — Dale Skalla

(57) ABSTRACT

Compositions and methods for producing a crop having a predetermined level of at least one primary trait of interest are provided. The compositions comprise seeds and plants exhibiting a primary trait of interest. Primary traits include traits that improve or otherwise facilitate the conversion of harvested plant material into a commercially useful product. The predetermined level of the primary trait is obtained by blending harvested plant material from at least two varieties of plants, wherein at least one of the varieties exhibits the primary trait. The blend can be customized for use in a variety of commercially important industrial or agricultural downstream uses.

8 Claims, 4 Drawing Sheets

METHODS FOR THE COMMERCIAL PRODUCTION OF TRANSGENIC PLANTS

CROSS REFERENCE TO RELATED APPLICATION

This application claims the benefit of U.S. Provisional Application Ser. No. 60/941,466, filed Jun. 1, 2007, the content of which is hereby incorporated in its entirety by reference herein.

FIELD OF THE INVENTION

This invention relates to plant molecular biology, particularly to methods and compositions for optimizing plant mixtures for obtaining commercially desirable harvested plant material.

BACKGROUND OF THE INVENTION

With the emergence of transgenic technologies, new ways to improve the agronomic performance of plants for food, feed, and processing applications have been devised. In addition, the ability to express foreign genes using transgenic technologies has opened up options for producing large quantities of commercially important products in plants.

New target genes of both plant and microbial origin are rapidly becoming available for the purpose of improving agronomic characteristic of crop species as well as plant properties. These advancements have already resulted in the development of plants with desirable traits such as resistance to diseases, insects, and herbicides, tolerance to heat and drought, reduced time to crop maturity, improved industrial processing, such as for the conversion of starch or biomass to fermentable sugars, and improved agronomic quality, such as high oil content and high protein content.

There is a need in the art to develop strategies for utilizing harvested plant material exhibiting a variety of traits requiring different target expression levels for optimizing the efficiency and productivity of plants used in commercial processes.

SUMMARY OF THE INVENTION

Provided herein are methods and compositions for producing a crop having a predetermined level ("target level") of at least one primary trait of interest. Primary traits of interest include any traits that improve or otherwise facilitate the conversion of harvested plant material into a commercially useful product. The predetermined level of the primary trait is obtained by blending harvested plant material from at least two varieties of plants, wherein at least one of the varieties exhibits the primary trait of interest. The blend can be customized for use in a variety of commercially important industrial or agricultural downstream uses.

In various embodiments, a seed blend is provided wherein seed from a first plant variety exhibiting at least one primary trait of interest is mixed with seed from at least a second plant variety that may exhibit at least one second primary trait of interest to achieve the desired level of the trait or traits in the crop or plant material harvested from the plants grown from the seed blend. The target level may be achieved by harvesting plant material grown from the premixed seed blend, or by individually planting seed from each variety at a target ratio and subsequently blending plant material harvested from each variety. The blend may exhibit a single primary trait of interest, or may collectively exhibit multiple primary traits of interest. Where multiple primary traits are present, multiple different varieties of plants may be used wherein each variety exhibits a different primary trait of interest, or wherein one or more varieties exhibit multiple traits of interest. One or more varieties in the blend may further exhibit one or more secondary traits of interest. Secondary traits of interest include traits that primarily are of benefit to a seed company, a grower, or a grain processor, for example, herbicide resistance, virus resistance, bacterial pathogen resistance, insect resistance and fungal resistance.

The seed and/or the grain exhibiting a primary trait of interest may be distinguishable from seed or grain not containing the primary trait of interest, and/or distinguishable from seed or grain containing a different primary trait of interest, based on seed coat color. Differential seed coat color may be the result of naturally occurring genetic variability, introduced trangenes encoding for a differential seed coat color, or through the external application of a dye or colorant to the seed or grain containing the different primary traits of interest.

DETAILED DESCRIPTION OF THE INVENTION

Figure 1A:
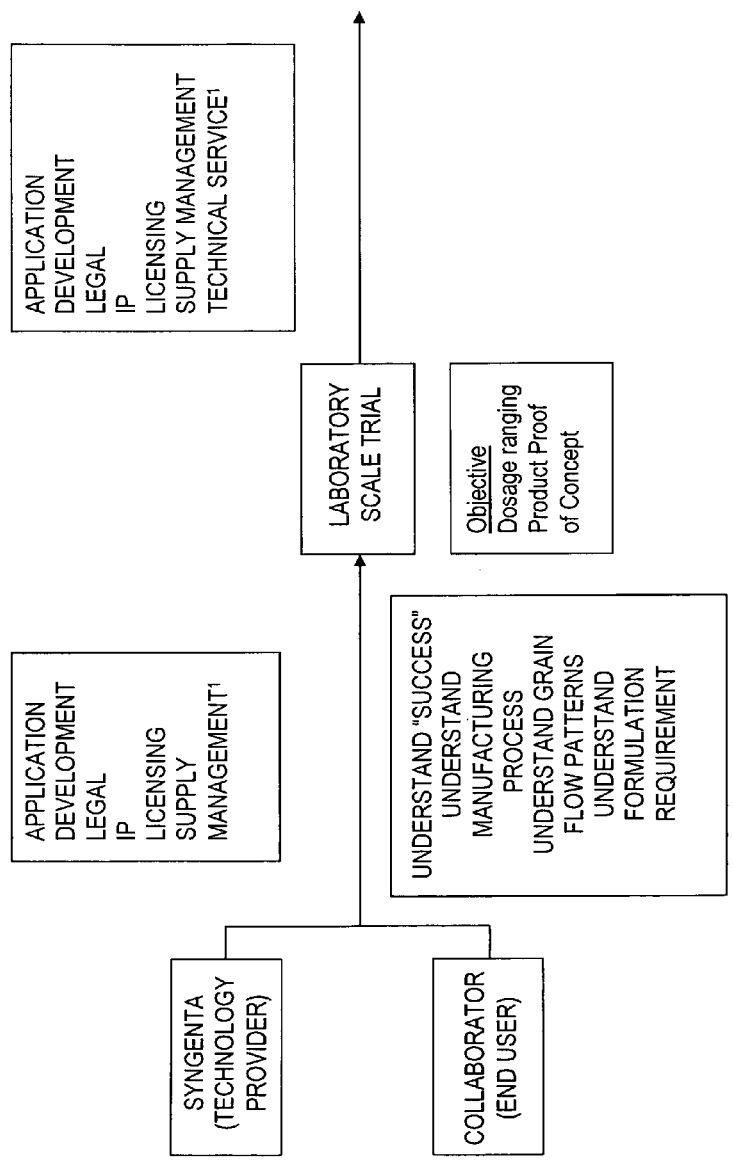
FIG. 1 provides a flow chart describing the general process utilized in the development of a seed blend producing a crop containing a target level of a trait of interest.
Figure 1B:
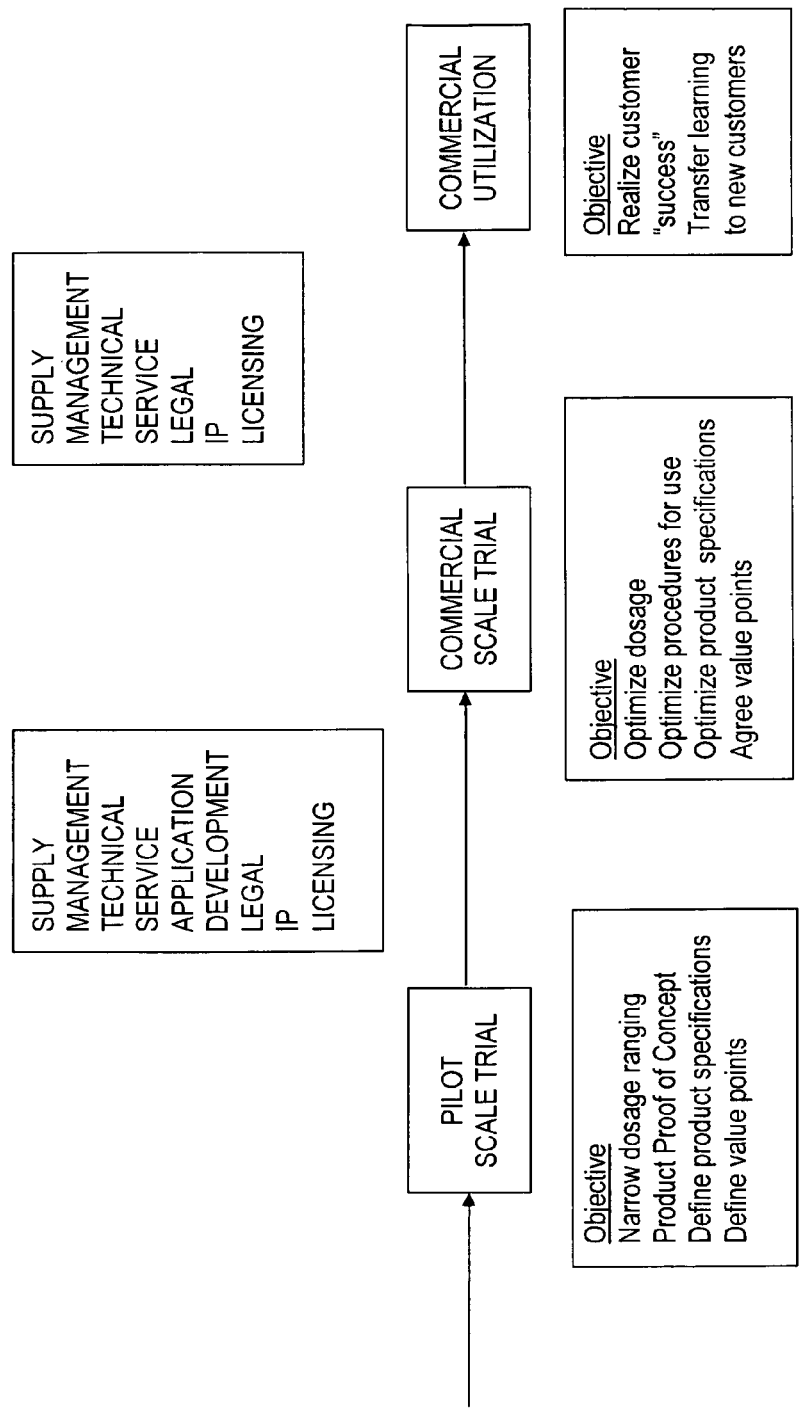

The methods of the invention find particular use in the integration of current practices for the cultivation of crop plants in a defined formulation for the purpose of obtaining a commercially desired harvested plant material that is optimized for a specific downstream use. For example, the harvested plant material can be used as a source of biomass for the production of fermentable sugars, or for agricultural and/or human consumption.

Plants having one or more primary traits of interest are planted in a field in a ratio to provide a predetermined percentage of the plants containing the trait(s) of interest in the total crop planted in the field. Harvesting of the total crop, or a representative proportion of the total crop, results in a blend of plant material in which the primary trait(s) of interest is present at an optimum level (i.e., "target level") for a particular downstream use. Downstream uses include industrial and agronomically useful products, including fermentation feedstocks, biofuel, animal feed, and human food. The "target ratio" refers to the percentage of plant material of each plant variety in the blend that is optimal to provide the predetermined level of the trait or traits of interest for the desired downstream use. As used herein, a "plant variety" refers to a taxonomic subdivision of a species of plants that has been created or selected intentionally and maintained, and that differs from the remainder of the species in certain characteristics. In the practices of the invention, the difference in the plant varieties grown from the seed blend may only be the primary trait or traits exhibited by each plant variety. However, it is not necessary that each plant variety in the blend be of the same species. In some embodiments, each plant variety in the blend is reproductively compatible with at least one other variety in the blend.

The target ratio of crop exhibiting the primary trait(s) of interest to crop not exhibiting the primary trait(s) of interest can be determined by performing a series of laboratory and field testing to determine the optimum level of primary trait(s) that is necessary for the intended downstream use. For the purposes of the present invention, a crop that "exhibits" a trait of interest is one that has a measurable level of that trait. For example, a crop exhibiting increased protein content has a measurable level of protein that is higher than that of a crop not exhibiting increased protein content. The measurement may be performed visually, mechanically, biologically, or chemically. Traits that result from the expression of a heterologous nucleic acid sequence (i.e., "transgenic" or "genetically engineered" plants) or traits that result from expression of an endogenous nucleic acid (i.e., naturally occurring, or introduced through breeding) can be measured by assessing the level of expression of that nucleic acid sequence, or measuring the level or activity of one or more endogenous plant genes, proteins and/or metabolites modulated by that nucleic acid sequence.

The target ratio of crop can be obtained by planting seeds provided in a premixed seed blend, by mixing seed at the target ratio at the time of planting, by separately planting seeds for each plant variety at the target ratio, or by mixing harvested plant material at the target ratio at or after the time of harvest. A "seed blend" refers to a mixture of seeds from two or more varieties of plants. When provided in a premixed composition, the seeds are blended at a predetermined level to obtain the target ratio of crop from the plants grown from the seed.

By a "crop plant" is intended any plant that is cultivated for the purpose of producing plant material that is sought after by man (a "crop") for either consumption by humans or agricultural animals, for biomass production for utilization in an industrial, pharmaceutical, or commercial process. The invention may be applied to any of a variety of plants, but are particularly useful for plants as described elsewhere herein.

As used herein, the term "plant part" or "harvested plant material" or "crop" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, tubers, rhizomes and the like. The term "seed" refers to the mature reproductive structure produced for the purpose of propagating the species and it is commonly sold to producers. The term "grain" comprises seed produced by growers for on-farm use or commercial distribution, in both cases for purposes other than growing or reproducing the species. The type of harvested plant material useful in the present invention depends on the downstream use.

As used herein, "biomass" refers to biological material collected and intended for further processing to isolate or concentrate a downstream product of interest. "Biomass" may comprise the fruit or parts of it or seeds, leaves, or stems or roots where these are the parts of the plant that are of particular interest for the industrial purpose. "Biomass," as it refers to harvested plant material, includes any structure or structures of a plant that contain or represent the product of interest.

The article "a" and "an" are used herein to refer to one or more than one (i.e., to at least one) of the grammatical object of the article. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Compositions

A. Seeds

The target level (or predetermined level) of a trait or traits of interest can be obtained by planting seeds provided in a premixed seed blend, by mixing seed at a target ratio at the time of planting, by separately planting seeds for each plant variety at the target ratio, or by mixing harvested plant material at the target ratio at or after the time of harvest. The "target ratio" refers to the ratio of seeds or ratio of harvested plant material of each variety in a blend necessary to achieve the target level of the trait or traits of interest. The "target level" includes the level of the trait of interest in a blend of harvested plant material (e.g., level of enzyme expression, level of protein content, level of oil content, level of vitamin content, etc) that is suitable, preferably optimal, for a particular downstream use. A "blend of harvested plant material" refers to a mixture of material obtainable from a plurality of plants where a percentage of these plants have one or more primary trait(s) of interest.

In one embodiment, the blend consists of harvested plant material from a first variety of plants exhibiting one or more primary trait(s) of interest and a second variety of plants that does not exhibit the primary trait(s) of interest. In another embodiment, the blend consists of harvested plant material from a first variety of plants exhibiting one or more primary traits of interest and a second variety of plants exhibiting one or more different primary trait(s) of interest. In another embodiment, the blend comprises harvested plant material from the first and the second varieties of plants as described above in addition to one or more additional varieties that either do not exhibit the primary trait(s) of interest, exhibit one or more different primary traits of interest, or that have one or more of the same primary trait(s) of interest as either the first or the second variety or both, or some combination thereof. It is contemplated that any combination of plants containing any number of primary traits of interest is useful in the present invention, so long as the final blend contains the primary trait(s) of interest at a level that is suitable, preferably optimal, for the downstream use. Any one or more of the varieties may further exhibit one or more secondary traits of interest as discussed elsewhere herein.

Thus, in one embodiment, the invention features an article of manufacture, comprising packaging material and plant seeds within the packaging material. The plant seeds can comprise about 0.1% to about 99.9%, including about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, and about 99%, seeds of a first variety and about 0.1 to about 99.1%, including about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, and about 99%, seeds of a second variety, wherein the sum of the percentage of each plant variety equals 100% of the total seed blend. Plants grown from seeds of the first variety exhibit one or more primary trait(s) of interest. Plants grown from seeds of the second variety may or may not exhibit the same primary trait of interest. In some embodiments, the second variety exhibits one or more different primary trait(s) of interest. In other embodiments, the second variety does not exhibit a primary trait of interest. The invention may further comprise about 0.1% to about 99.8%, including about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 97%, about 98%, and about 99%, seeds of one or more additional varieties, which may or may not contain a primary trait of interest. The seeds are blended at the target ratio, planted in a field, and plant material harvested from the plants has the target level of the primary trait(s) of interest.

In one embodiment, the article of manufacture comprising a substantially uniform mixture of seeds of each of the varieties is conditioned and bagged in packaging material by means known in the art. The seed is blended at a target ratio at the seed processing facility. Such a bag of seed preferably has a package label accompanying the bag, e.g., a tag or label secured to the packaging material, a label printed on the packaging material or a label inserted within the bag. The package label indicates that the seeds therein are a mixture of varieties, e.g., two or more different varieties. The package label may indicate that plants grown from such seeds possess one or more primary and/or secondary trait(s) of interest. The package label also may indicate that the seed mixture contained therein permits detection of seed containing the trait of interest prior to planting and/or when harvested.

In another embodiment, the article of manufacture, comprising packaging material and plant seeds within the packaging material, consists of a single variety of plant seed. Seeds of each variety necessary to produce the final blend of harvested plant material are packaged separately and provided to the grower. A "grower" is the person responsible for planting, maintaining and harvesting a crop. Further provided are instructions to the grower defining the target ratio of seeds to be planted in the field. The seeds are mixed at the target ratio by the grower prior to planting by any suitable mechanical means, and the blended seed is planted in the field. Alternatively, the seeds can be planted in the field using planting equipment capable of segregating the seeds of each variety (e.g., a 12-row planter, a 16-row planter, a skip-row planter, etc.). The target ratio is achieved by planting the seeds from each variety in different rows wherein the number of rows of each variety is dependent on the number of plants of each variety that is necessary to achieve the target level of the primary trait(s) of interest in the harvested plant material. In this example, the harvested plant material can be combined as it is harvested and brought into the processing and drying facility as a blend containing the target level of the primary trait(s) of interest.

Alternatively, the plant material or crop from each variety can be harvested independently. The harvested plant material can be combined at the target ratio at the unloading facility or at the processing or drying facilities. In this embodiment, it is not necessary to plant seeds from each variety at any particular ratio, so long as the plant material from each variety is harvested separately, and that the harvested plant material is blended at the predetermined target ratio. It is also not necessary to harvest plant material from each of the varieties at the same time during the growing season, unless the harvested plant material is to be blended at the time of harvest (i.e., in the field).

A seed composition can be formulated in a quantity of about 0.1 kilograms (kg) or more, about 0.5 kg or more, about 1 kg or more, about 5 kg or more, about 10 kg or more, about 20 kg or more, about 35 kg or more, about 100 kg or more, about 1,000 kg or more, about 10,000 kg or more, or about 50,000 kg or more. The seeds can be provided to the grower in a common delivery unit, for example, a seed bag, a bulk seed bag, a bulk seed container (e.g., a Q-bit container), a bulk seed delivery trailer, and the like. Where the seeds are pre-mixed at the seed processing facility, seeds for each variety are contained in the same common delivery unit. Where the seeds are mixed at the time of planting, each variety is provided in one or more individual common delivery units.

Seed material is customarily treated with a protectant coating comprising herbicides, insecticides, fungicides, bactericides, nematicides, molluscicides, or mixtures thereof. Customarily used protectant coatings comprise compounds such as captan, carboxin, thiram (TMTD®), methalaxyl (APRON®), and pirimiphos-methyl (ACTELLIC®). If desired, these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

In each of these embodiments, the first variety in a seed composition exhibits one or more primary trait(s) of interest. The additional varieties of seeds in the blend may exhibit the same trait(s) as the first variety, may exhibit one or more different primary trait(s) of interest, or may not exhibit any of the primary trait(s) of interest. Primary traits of interest include any traits that improve or otherwise facilitate the conversion of harvested plant material into a commercially useful product, including, for example, increased or altered carbohydrate content and/or distribution, improved fermentation properties, increased oil content, increased protein content, improved digestibility, and increased nutraceutical content, e.g., increased phytosterol content, increased tocopherol content, increased stanol content or increased vitamin content. Primary traits of interest also include, for example, a reduced content of an unwanted component in a harvested crop, e.g., phytic acid, soybean trypsin inhibitor, or starch degrading enzymes, depending on the downstream use. Varieties possessing a gene(s) for a specialty trait have a statistically significant increase or decrease in the trait relative to a variety that does not possess or does not express those gene(s).

One or more varieties may exhibit one or more secondary trait(s) of interest. Secondary traits of interest include traits that primarily are of benefit to a seed company, a grower, or a grain processor, for example, herbicide resistance, virus resistance, bacterial pathogen resistance, insect resistance and fungal resistance. See, e.g., U.S. Pat. Nos. 5,569,823; 5,304,730; 5,495,071; 6,329,504; and 6,337,431. A secondary trait of interest may also be one that increases plant vigor or yield (including traits that allow a plant to grow at different temperatures, soil conditions and levels of sunlight and precipitation), or one that allows identification of a plant exhibiting a trait of interest (e.g., selectable marker gene, seed coat color, etc.). Varieties possessing a gene(s) for a secondary trait of interest have a statistically significant increase or decrease in the trait relative to a variety that does not possess or does not express those gene(s). Primary and/or secondary traits of interest can be due to one or more naturally occurring variant genes, one or more transgenes, or a combination of naturally occurring variant gene(s) and transgene(s).

B. Use

The invention also features a method for producing a crop or harvested plant material having a predetermined level of one or more primary trait(s) of interest. The method comprises harvesting a crop grown from a group of crop plants comprising about 0.1% to about 99.9% seeds of a first variety and about 0.1 to about 99.9% seeds of one or more additional varieties. Plants of at least one variety exhibit a primary trait. The harvested plant material from each variety is present in the final crop at ratio that results in the primary trait(s) of interest being present at a target level (i.e., the "target ratio"), where the target level is optimized for the downstream use of the crop or harvested plant material. Downstream uses include agronomical and industrial uses, for example, human food, animal feed, biofuel, industrial alcohol, fermentation feedstocks, etc.

The soluble carbohydrates produced by blending the harvested plant material of the present invention will include fermentable carbohydrates, which can then be used as fermentation feedstocks for ethanol, ethanol-containing beverages (such as malted beverages and distilled spirits), and other fermentation products such as foods, nutraceuticals, enzymes and industrial materials. The methods for fermentation using plant-derived carbohydrate feedstocks are well known to those skilled in the art, with established processes for various fermentation products (see for example Vogel et al. 1996, Fermentation and Biochemical Engineering Handbook: Principles, Process Design, and Equipment, Noyes Publications, Park Ridge, N.J., USA and references cited therein). In one embodiment, the soluble carbohydrates may be extracted by crushing the plant, or by diffusion from the plant tissues into water or another suitable solvent. The resulting juice or extract containing the soluble carbohydrates may be used directly as a substrate for fermentation or bioconversion in a batch, continuous, or immobilized-cell process. Alternatively, part of the soluble carbohydrates may be recovered for other uses and the unrecovered components used as fermentation feedstocks, as in the case of molasses remaining after recovery of most of the sucrose by crystallization.

The harvested plant material of the invention can be used to formulate food or beverage for human consumption or animal feed, can be used to formulate diet with easily digestible starch and hence more extractable energy, or can be used to improve the nutritional quality of the food or feed (e.g., increased vitamin content, increased oil content, increased protein content, etc). The food, feed, or beverage can be flour, dough, bread, pasta, cookies, cake, thickener, beer, malted beverage, or a food additive. The food, feed, or beer product of can have reduced allergenicity and/or increased digestibility. Further, a dough product can have increased strength and volume in comparison to a dough made from a non-transgenic seed or grain of the same species. The food, feed, or beverage can have hyperdigestible protein and/or hyperdigestible starch. The food, feed, or beverage can be hypoallergenic.

Oil extracted from the harvested plant material of the invention can be used as a raw material for chemical modification, a component of biodegradable material, a component of a blended food product, a component of an edible oil or cooking oil, lubricant or a component thereof, biodiesel or a component thereof, a component of a snack food, a fermentation process raw material, or a component of cosmetics.

The harvested plant material of the invention can also be combined with other ingredients to produce a useful product. The specific ingredients included in a product will be determined according to the ultimate use of the product. Exemplary products include animal feed, raw material for chemical modification, biodegradable materials, blended food product, edible oil, cooking oil, lubricant, biodiesel process raw material, snack food, cosmetics, cleaning and detergent compositions (e.g., laundry detergents, dish washing detergents, and hard surface cleaning compositions), and fermentation process raw material. Products incorporating the harvested plant material described herein also include complete or partially complete swine, poultry, and cattle feeds, pet foods, and human food products such as extruded snack foods, breads, as a food binding agent, aquaculture feeds, fermentable mixtures, food supplements, sport drinks, nutritional food bars, multi-vitamin supplements, diet drinks, and cereal foods. Products incorporating the harvested plant material described herein include, e.g., cardboard, paper products, and industrial materials. These products may incorporate the raw harvested plant material, or may incorporate a processed or extracted form of the harvested plant material (e.g., oil, protein, starch, etc. extracted from the harvested plant material).

C. Primary Trait of Interest

Primary traits of interest include any traits that improve or otherwise facilitate the conversion of harvested plant material into a commercially useful product, including, for example, increased or altered carbohydrate content and/or distribution, improved fermentation properties, increased oil content, increased protein content, improved digestibility, and increased nutraceutical content, e.g., increased phytosterol content, increased tocopherol content, increased stanol content or increased vitamin content. Primary traits of interest also include, for example, a reduced content of an unwanted component in a harvested crop, e.g., phytic acid, soybean trypsin inhibitor, or starch degrading enzymes, depending on the downstream use. Primary traits of interest can be due to one or more naturally occurring variant genes, one or more transgenes, or a combination of naturally occurring variant gene(s) and transgene(s). A primary trait of interest can be realized in a plant not otherwise exhibiting that trait through the heterologous expression of a nucleic acid sequence (i.e., "transgene") associated with that trait. By "associated with a trait of interest" is intended that the nucleic acid sequence can directly or indirectly contribute to the existence of a trait of interest (e.g., increasing cellulose degradation by the heterologous expression of a starch degrading enzyme or increasing starch accumulation by the heterologous expression of an antisense nucleic acid sequence that inhibits the activity of a starch degrading enzyme).

One example of a primary trait of interest includes improved digestibility and/or nutritional compositions. To achieve this trait, a polypeptide or enzyme exhibiting "phytase" activity or a "phytase" can be heterologously expressed in a plant of the invention to improve plant digestibility and to improve the food and feed utilization or its conversion efficiency (i.e. by improving the bioavailability of proteins and minerals, or increasing the absorption thereof, which would otherwise have been bound by phytate). Phytases (myo-inositol hexakisphosphate phosphohydrolase: EC 3.1.3.8) are enzymes that hydrolyze phytate (myo-inositol hexakisphosphate) to myo-inositol and inorganic phosphate. Among the polypeptides particularly useful for the practice of this invention include, but are not limited to, D-myo-inositol-3-phosphate synthase, myo-inositol 1-phosphate synthase (otherwise referred to as INO1), phosphatidylinositol-4-phosphate-5-kinase, signaling inositol polyphosphate-5-phosphatase (SIP-110), myo-inositol monophosphatase-3, myo-inositol 1,3,4 triphosphate 5/6 kinase, 1 D-myo-inositol trisphosphate 3-kinase B, myo-inositol monophosphatase-1, inositol polyphosphate 5-phosphatase, 1 D-myo-inositol trisphosphate 3-kinase, phosphatidylinositol 3-kinase, phosphatidylinositol 4-kinase, phosphatidylinositol synthase, phosphatidylinositol transfer protein, phosphatidylinositol 4,5-bisphosphate 5-phosphatase, myo-inositol transporter, phosphatidylinositol-specific phospholipase C and maize phytase.

Improved digestibility and improved nutrient availability can also be achieved in a plant by reducing the extent of disulfide bonding (see WO 00/36126, filed 15 Dec. 1999). Expression of transgenic thioredoxin reductase provides a method for reducing the disulfide bonds in seed proteins during or prior to industrial processing (see WO0058453). Grain harvested from these plants have altered storage protein quality and perform qualitatively differently from normal grain during industrial processing or animal digestion (both referred to subsequently as "processing"). Increasing thioredoxin activity through expression of transgenic thioredoxin reductase also increases protein solubility, and thus increases yield, in the water-soluble protein fractions. Therefore, expression of transgenic thioredoxin reductase is a means of altering the quality of the material (seeds) going into grain processing, altering the quality of the material derived from grain processing, maximizing yields of specific seed components during processing (increasing efficiency), changing processing methods, and creating new uses for seed-derived fractions or components from milling streams.

Further, plants expressing a heterologous xylanase enzyme result in a primary trait of interest that includes improved digestibility for food or feed. Xylanases are hemicellulolytic enzymes that improve the breakdown of plant cell walls which leads to better utilization of the plant nutrients by the animal. This leads to improved growth rate and feed conversion. Also, the viscosity of the feeds containing xylan can be reduced.

Numerous xylanases from fungal and bacterial microorganisms have been identified and characterized. (See, e.g., U.S. Pat. No. 5,437,992; Coughlin, M. P.; Biely, P. et al., Espoo 1993; P. Souminen and T. Reinikainen eds., Foundation for Biotechnical and Industrial Fermentation Research 8:125-135 (1993); U.S. Patent Application Publication No. 2005/0208178; and WO03/16654). In particular, three specific xylanases (XYL-I, XYL-II, and XYL-III) have been identified in *T. reesei* (Tenkanen, et al., Enzyme Microb. Technol. 14:566 (1992); Torronen, et al., Bio/Technology 10:1461 (1992); and Xu, et al., Appl. Microbiol. Biotechnol. 49:718 (1998)).

It is also possible to modify polysaccharide composition by the introduction and translation of one or more genes encoding a polysaccharide degrading enzyme. Such plants may be useful for generating, for example, fermentation feedstocks. Enzymes associated with this primary trait of interest include: starch degrading enzymes such as α-amylases (EC 3.2.1.1), glucuronidases (E.C. 3.2.1.131); exo-1,4-α-D glucanases such as amyloglucosidases and glucoamylase (EC 3.2.1.3), β-amylases (EC 3.2.1.2), α-glucosidases (EC 3.2.1.20), and other exo-amylases; and starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-β-D-glucanase (EC 3.2.1.39), β-glucosidase (EC 3.2.1.21), endo-1,4-β-glucanase (EC 3.2.1.4) and the like; c) endoglucanases such as endo-1,3-β-glucanase (EC 3.2.1.6); d) L-arabinases, such as endo-1,5-α-L-arabinase (EC 3.2.1.99), α-arabinosidases (EC 3.2.1.55) and the like; e) galactanases such as endo-1,4-β-D-galactanase (EC 3.2.1.89), endo-1,3-β-D-galactanase (EC 3.2.1.90), α-galactosidase (EC 3.2.1.22), β-galactosidase (EC 3.2.1.23) and the like; f) mannanases, such as endo-1,4-β-D-mannanase (EC 3.2.1.78), β-mannosidase (EC 3.2.1.25), α-mannosidase (EC 3.2.1.24) and the like; g) xylanases, such as endo-1,4-β-xylanase (EC 3.2.1.8), β-D-xylosidase (EC 3.2.1.37), 1,3-β-D-xylanase, and the like; h) other enzymes such as α-L-fucosidase (EC 3.2.1.51), α-L-rhamnosidase (EC 3.2.1.40), levanase (EC 3.2.1.65), inulanase (EC 3.2.1.7), and the like.

Additional genes associated with a primary trait of interest include those encoding enzymes capable of further degrading the maltose maltotriose and α-dextrins obtained from the first degradation of starch, include maltases, α-dexitrinase, α-1,6-glucosidases, glucoamylases (α-1,4-glucan glucohydrolases), and the like. The action of these enzymes results in the formation of glucose.

In yet a further embodiment of the present invention, if desired, one or more further secondary enzymes, which are capable of modifying monosaccharides, may be expressed in one or more varieties present in the blend of the invention. Such enzymes include but are not limited to glucose isomerase, invertase, and the like.

An additional primary trait of interest includes an increase in starch accumulation in plants. The rate of starch synthesis is largely determined by the activity of AGPase, the first enzyme in the pathway. The form of this enzyme found in leaves is activated by 3-phosphoglyceric acid (3-PGA), a product of photosynthesis, and inhibited by inorganic phosphate ($P_i$), which accumulates when the rate of photosynthesis declines. This causes starch production to be increased at times when photosynthesis is proceeding rapidly and there are surplus sugars to be stored, and decreased during leaner times. Mutant and bacterial AGPase enzymes have been identified which are not sensitive to 3-PGA and $P_i$, thus bypassing the regulatory mechanism controlling starch degradation (U.S. Pat. Nos. 7,098,380 and 6,617,495). Heterologous expression of these enzymes in plants can result in the accumulation of starch in the plant.

Of particular interest in the harvested plant material of the present invention is the expression of heterologous starch degrading enzymes such as glucoamylase and amylase in the harvested plant material for downstream use in, for example, ethanol production. Glucoamylases (α-1,4-glucan glucohydrolases, E.C.3.2.1.3.) are starch hydrolyzing exo-acting carbohydrases. Glucoamylases catalyze the removal of successive glucose units from the non-reducing ends of starch or related oligo and polysaccharide molecules and can hydrolyze both linear and branched glucosidic linkages of starch (amylose and amylopectin). Commercially glucoamylases are very important enzymes that have been used in a wide variety of applications requiring the hydrolysis of starch. Glucoamylases can be provided through the heterologous expression of glucoamylase in at least one variety in the harvested plant material of the invention.

Glucoamylases are used for the hydrolysis of starch to produce high fructose corn sweeteners. In general, starch hydrolyzing processes involve the use of alpha amylases to hydrolyze the starch to dextrins and glucoamylases to hydrolyze the dextrins to glucose. The glucose is then converted to fructose by other enzymes such as glucose isomerases. Glucose produced by glucoamylases can also be crystallized or used in fermentations to produce other end-products, such as citric acid, ascorbic acid, glutamic acid, 1,3 propanediol and others. Glucoamylases are used in alcohol production, such as beer production and sake production. Glucoamylases also find use in the production of ethanol for fuel and for consumption. Recently, glucoamylases have been used in low-temperature processes for the hydrolysis of granular (non-cooked) starch. Glucoamylases are also used in the preparation of animal feeds as feed additives or as liquid feed components for livestock animals.

The term "alpha-amylase (e.g., E.C. class 3.2.1.1)" refers to enzymes that catalyze the hydrolysis of alpha-1,4-glucosidic linkages. These enzymes have also been described as those effecting the exo or endohydrolysis of 1,4-α-D-glucosidic linkages in polysaccharides containing 1,4-α-linked D-glucose units. Another term used to describe these enzymes is "glycogenase". Exemplary enzymes include alpha-1,4-glucan 4-glucanohydrase glucanohydrolase.

In one embodiment, a first crop expresses glucoamylase, and a second crop expresses alpha-amylase. The crop may optionally comprise one or more additional varieties. The one or more additional varieties may exhibit a third primary trait of interest, may exhibit no primary trait of interest, or may serve as a marker plant. An additional variety included in this harvested plant material may include a high starch plant that results, for example, from the expression of mutant or bacterial AGPase.

Naturally-occurring genetic variability in plants with altered starch metabolism are also useful in the blended plant material of the invention. Many such plants carry mutations in genes encoding isoforms of starch synthesis or starch degradation enzymes. For example, plants have been identified which are heterozygous or homozygous for one or more of the waxy (wx), amylose extender (ae), dull (du), horny (h), shrunken (sh), brittle (bt), floury (fl), opaque (o), or sugary (su) mutant alleles. See, for example, U.S. Pat. Nos. 4,428,972; 4,767,849; 4,774,328; 4,789,738; 4,789,557; 4,790,997; 4,792,458; 4,798,735; and 4,801,470, herein incorporated by reference. These plants can be used in their native form, or can be modified to exhibit one or more additional primary traits of interest.

Further additional enzymes which may be used include proteases, such as fungal and bacterial proteases. Fungal proteases include, for example, those obtained from *Aspergillus, Trichoderma, Mucor* and *Rhizopus*, such as *A. niger, A. awamori, A. oryzae* and *M. miehei*. Other enzymes include, but are not limited to, cellulases, such as endoglucanases and cellobiohydrolases; hemicellulases, such as mannases and arabinofuranosidases (EC 3.2.1.55); lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g. E.C. 3.1.1.74).

It is also an object of the present invention to provide harvested plant material that will provide a target level of two or more traits of interest for use in multiple downstream applications. For example, a portion of the plant material will exhibit improved feed characteristics (e.g., improved digestibility, improved nutrient content, and the like) and one or more additional varieties will exhibit improved liquefaction for use in, for example, ethanol conversion. It is contemplated that any combination of plant varieties exhibiting any number of traits of interest may be useful in the methods of the present invention, so long as the varieties are present in the crop at a target ratio that is optimal for achieving the target level of each of the traits of interest.

The source from which DNA sequences encoding these enzymes may be obtained is not relevant, provided the enzyme is active in the environment in which the enzyme is expressed or in which the expressed enzyme is targeted. The choice of enzymes may depend on the substrate specificity and/or the desired end-product for downstream use (e.g., enzymes with improved properties such as thermostability, acid stability, and the like).

D. Secondary Traits of Interest

One or more varieties may exhibit one or more secondary trait(s) of interest. Secondary traits of interest include agronomic traits that primarily are of benefit to a seed company, a grower, or a grain processor, for example, herbicide resistance, virus resistance, bacterial pathogen resistance, insect resistance, nematode resistance, and fungal resistance. See, e.g., U.S. Pat. Nos. 5,569,823; 5,304,730; 5,495,071; 6,329,504; and 6,337,431. A secondary trait of interest may also be one that increases plant vigor or yield (including traits that allow a plant to grow at different temperatures, soil conditions and levels of sunlight and precipitation), or one that allows identification of a plant exhibiting a trait of interest (e.g., selectable marker gene, seed coat color, etc.).

In some embodiments, one or more of the plant varieties in a seed composition of the invention exhibit resistance to an herbicide. A number of genes are available, both transgenic and non-transgenic, that confer herbicide resistance. Herbicide resistance is also sometimes referred to as herbicide tolerance. Genes conferring resistance to a herbicide that inhibits the growing point or meristem, such as an imidazalinone or a sulfonylurea can be suitable. Exemplary genes in this category code for mutant ALS and AHAS enzymes as described, for example, in U.S. Pat. Nos. 5,767,366 and 5,928,937. U.S. Pat. Nos. 4,761,373 and 5,013,659 are directed to plants resistant to various imidazolinone or sulfonamide herbicides. U.S. Pat. No. 4,975,374 relates to plant cells and plants containing a gene encoding a mutant glutamine synthetase (GS) resistant to inhibition by herbicides that are known to inhibit GS, e.g. phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Genes for resistance to glyphosate are also suitable. See, for example, U.S. Pat. No. 4,940,835 and U.S. Pat. No. 4,769,061. U.S. Pat. No. 5,554,798 discloses transgenic glyphosate resistant maize plants, which resistance is conferred by an altered 5-enolpyruvyl-3-phosphoshikimate (EPSP) synthase gene.

Genes for resistance to phosphono compounds such as glufosinate ammonium or phosphinothricin, and pyridinoxy or phenoxy propionic acids and cyclohexones are also suitable. See European application No. 0 242 246. See also, U.S. Pat. Nos. 5,879,903, 5,276,268 and 5,561,236.

Other suitable herbicides include those that inhibit photosynthesis, such as a triazine and a benzonitrile (nitrilase). See U.S. Pat. No. 4,810,648. Other suitable herbicides include 2,2-dichloropropionic acid, sethoxydim, haloxyfop, imidazolinone herbicides, sulfonylurea herbicides, triazolopyrimidine herbicides, s-triazine herbicides and bromoxynil. Also suitable are genes that confer resistance to a protox enzyme, or provide enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. See, e.g., U.S. Patent Application No. 20010016956, and U.S. Pat. No. 6,084,155.

The insecticidal proteins useful for the invention may be expressed in one or more varieties in the harvested plant material in an amount sufficient to control insect pests, i.e. insect controlling amounts. It is recognized that the amount of expression of insecticidal protein in a plant necessary to control insects may vary depending upon species of plant, type of insect, environmental factors and the like. Genes useful for insect or pest resistance include, for example, genes encoding toxins identified in *Bacillus* organisms. Genes encoding *Bacillus thuringiensis* (Bt) toxins from several subspecies have been cloned and recombinant clones have been found to be toxic to lepidopteran, dipteran and coleopteran insect larvae (for example, various delta-endotoxin genes such as Cry1Aa, Cry1Ab, Cry1Ac, Cry1B, Cry1C, Cry1D, Cry1Ea, Cry1Fa, Cry3A, Cry9A, Cry9C and Cry9B; as well as genes encoding vegetative insecticial proteins such as Vip1, Vip2 and Vip3). A full list of Bt toxins can be found on the worldwide web at www.lifesci.sussex.ac.uk/home/Neil_Crickmore/Bt/.

The secondary traits of interest in the present invention are useful for controlling a wide variety of insects including but not limited to corn earworm, rootworms, cutworms, armyworms, particularly fall and beet armyworms, wireworms, aphids, corn borers, particularly European corn borers, sugarcane borer, lesser corn stalk borer, Southwestern corn borer, etc.

For various other reasons, particularly management of potential insect resistance developing to plant expressed insecticidal proteins, it is beneficial to express more than one insecticidal protein (IP) in the same plant. One could express two different genes (such as genes encoding two different *Bacillus thuringiensis* derived delta-endotoxins which bind different receptors in the target insect's midgut) in the same tissues, or one can selectively express the two toxins in different tissues of the same plant using tissue specific promoters. Likewise, a plant may be transformed with constructs encoding more than one type of insecticidal protein to control various insects. Thus, a number of variations may be constructed by one of skill in the art.

E. Seed Coat

An additional secondary trait useful in the plants of the present invention is seed coat color. The "seed coat" is the remnants of the outer integuments of a plant flower in dicot plants or the pericarp in monocot plants, and as such is genetically identical to the plant on which the seed is borne. This "marker seed" can be used to denote the presence of a plant variety exhibiting a primary trait of interest, or to distinguish seed containing the primary trait of interest from seed not containing the primary trait of interest, and/or from seed containing a different primary trait of interest. The seed coat color can be associated with a heritable gene encoding seed coat color, or can be applied to the seed at the seed processing facility or to the harvested grain at the processing facility, or any combination thereof. Where the seed coat color is heritable, the marker seed should exhibit the same herbicide resistance, and preferably the same pest resistance, resistance as the other varieties in the blend to ensure its propagation. A gene encoding seed coat color can be genetically linked to a gene associated with the primary trait of interest (e.g., under the control of the same promoter) and thereby expressed in the variety that exhibits the trait of interest, can be expressed in a variety that exhibits the trait of interest without being genetically linked to the gene associated with the primary trait (e.g., integrated into a distant site in the plant genome from the gene associated with the trait), or can be expressed in a variety that does not exhibit the trait of interest. Therefore, the harvested plant material can comprise a first variety exhibiting a primary trait of interest, a second variety exhibiting no or a different primary trait of interest, and a third variety that does not exhibit the primary trait of interest but does have a different seed coat color.

In one embodiment, seed coat color can be obtained by selecting varieties in which to introduce the trait of interest. Within some plant species there are cultivars bearing different colored seed coats. For example in soybeans there are two genes determining the color of the seeds. Seeds are either black, brown, yellow or speckled dark on a lighter background depending on the recessive/dominant relationship of the genes. Thus, the use of a variety with colored seed coats (black or brown or speckled in the case of soybeans) for a transgenic platform will allow distinction of any transgenic seeds within a larger quantity of seeds. In the context of seed coat color, the term "transgenic" refers to any plant or plant part in which a heterologous gene has been introduced. The transgenic plant may be transgenic for either a primary or a secondary trait of interest, or both.

One can also create transgenic plants having a distinguishable seed coat color by the routine introduction of heterologous genes into these plant varieties that give rise to seeds having colors selected from the group consisting of: blue; red; red, white and blue; plum; maroon; chinmark; deep purple; pink, rose to dark rose; orange; and various combinations of these colors that will allow distinction of any transgenic seeds within a larger quantity of seeds.

Seed color may be measured using a Technicon visible light reflectance spectrophotometer (VLS) calibrated to determine total light reflectance from 400 to 800 nanometers. This wavelength setting allows separation of yellow from brown from black seeds. Alternatively, optical scanning technology can be used to distinguish seeds on the basis of color. Both VLS and optical scanning can be set up for high-throughput analysis.

In another embodiment, seed color can be obtained by the surface addition of seed coat colorants such as microparticles. Microparticles are used to mark one or more varieties in a seed composition. Microparticles adhered to individual seeds of a particular variety permit ready identification of that variety. A specific series of microparticle types can be used, each series adhered to seeds of a particular variety. Alternatively, a single type of microparticles can be used, such a type adhered to seeds of only one of the varieties in a seed composition. In some embodiments, seeds of at least one of the varieties has a seed coat color that differs from at least one other of the varieties, e.g., seeds of the first and third varieties have the same seed coat color and seeds of the second variety have a seed coat color that differs from the seed coat color of the first and third varieties. In some embodiments, it is not necessary for all of the seeds of a particular variety to be marked in this manner. Rather, a proportion of the seeds in that variety can be marked to denote the presence of a transgenic seed within that batch of seed.

In another embodiment, seed coat colorant is added to the harvested grain in a manner in which grain containing the primary trait of interest is distinguishable from grain not containing the trait of interest, and/or from the grain containing a different trait of interest. In yet another embodiment, seed coat colorant is applied to all of the grain harvested for the blend so that the trait-containing and non trait-containing grain is indistinguishable.

Microparticles having a single colored layer can be used, recognizing that certain colors may not be suitable for particular seed coat colors. For example, a tan microparticle would render identification difficult if the marked variety had a tan seed coat color. Microparticles having two colored layers can be used. Dual layer microparticles can often provide a sufficient diversity of color combinations. Alternatively, a 5-layered particle can be used. If desired, microparticles can include visual enhancers. Suitable visual enhancers include, without limitation, pearlescent colorant, glitter, metal flake pigments and glass microspheres. Visual enhancers can provide microparticles with a higher localized reflectance and a more characteristic appearance, making the colored layer(s) of a microparticle more easily distinguishable. Visual enhancers can also further differentiate color layers of one type of microparticle from another type of microparticle. For example, a visual enhancer can be added to distinguish one secondary color (i.e., orange, green, and purple) from another secondary color.

Microparticles can be combined with a binder, for instance an adhesive or coating formulation. Suitable binder materials are known. The resulting particle/adhesive mixture can, for example, then be applied to the surface of individual seeds for identification purposes.

A marked seed(s) can be observed to determine the presence or absence of microparticles. If the microparticles are visible to the naked eye, the examination may be performed without additional equipment. For microparticles that are not easily visualized by the naked eye, equipment such as a light microscope or a magnifying glass may be used. Typically, microparticles can be examined using a common 40× or 100× microscope.

As an alternative to visually distinguishable characteristics, the layer(s) of different types of microparticles may be distinguished by machine-readable characteristics. Machine-readable characteristics can include magnetic characteristics, infrared or ultraviolet absorption characteristics, infrared or ultraviolet reflection characteristics, or fluorescence or visible light transmission characteristics. Alternatively, or in addition, one or more varieties of seed (or any proportion thereof) may contain a distinguishable inert molecular tag such as the halogen-substituted benzenes linked to tag-liner tert-butyl esters described, for example, in Orlenmeyer et al. (1993) *Proc. Natl. Acad. Sci. USA* 90:10922-10926 and U.S. Pat. No. 6,338,945, each of which is herein incorporated by reference in its entirety. In this embodiment, one variety of seed contains a unique tag that is detected, for example, using gas chromatographic, UV, visual light and NIR and other spectroscopic methods. Other variet(ies) in the blend may contain a different molecular tag, or may contain no molecular tag at all. Another alternative to visually distinguishing trait containing from non-trait containing grain or seed is the inclusion of radio frequency identity devices (RFID) and/or glass microbarcodes [Dejneka et al. (2003) PNAS 100 (2), 389] into the harvested seed or grain. These RFID and/or glass microbarcodes may be manually included in the seed or grain delivery container to identify trait-containing seed in examples above. RFID and/or glass microbarcodes may also be used to identify harvested plant material containing the primary trait(s) of interest. In either instance, a RFID and/or glass microbarcodes reader may be used to differentiate the trait-containing seed or grain.

F. Plants

Plants useful in the present invention include plants that are transgenic for at least a gene associated with the primary trait of interest, as well as plants exhibiting the primary trait of interest due to the presence of a naturally-occurring gene or a gene arising through natural variation or mutation of an endogenous gene associated with the trait. These plants can be obtained through commercial sources, or can be generated using the transformation methods described herein. Plants that do not exhibit a primary trait of interest may also be included in the harvested plant material at a predetermined level (e.g., the target ratio for that variety).

The type of plant selected depends on a variety of factors, including for example, the downstream use of the harvested plant material, amenability of the plant species to transformation, and the conditions under which the plants will be grown, harvested, and/or processed. One of skill will further recognize that additional factors for selecting appropriate plant varieties for use in the present invention include high yield potential, good stalk strength, resistance to specific diseases, drought tolerance, rapid dry down and grain quality sufficient to allow storage and shipment to market with minimum loss. While it is not necessary to use the same hybrid (or variety) of plant for the trait and non trait containing plants, it is preferable to use varieties with the same height and pollination time. However, it is also contemplated that varieties that differ in height and/or pollination time can be used to optimize the target level of the trait(s) of interest in the final harvested plant material.

For plants with increased nutritional quality, several varieties of corn are available, such as those with increased lysine (Crow's Hybrid Corn Company, Milford, Ill.), protein (BASF) and oil (Pfister Hybrid Corn Company, El Paso, Ill. under the trademark KERNOIL®) levels. Other suitable high oil corn includes the corn populations known as Illinois High Oil (IHO) and Alexander High Oil (Alexo), samples of which are available from the University of Illinois Maize Genetics Cooperative—Stock Center (Urbana, Ill.).

Sweet corn is also available in which there is a reduction in the amount of starch and an increase in the amount of glucose, sucrose and/or water soluble polysaccharides normally found in the immature corn kernel (Creech, R. and Alexander, D. E. In Maize Breeding and Genetics; D. B. Walden, Ed.; John Wiley and Sons: New York, 1978; pp. 249-264). In several plant species such as corn (Shannon & Garwood, 1984), pea (Bhattacharyya et al., 1990), potato (Hovenkamp-Hermelink et al., 1987), *Arabidopsis* (Caspar et al., 1985; Lin et al., 1988a; Lin et al., 1988b) and tobacco (Hanson et al., 1988), mutants with an altered carbohydrate composition have been found. Brown mid rib (Bmr) corn has been used as an alternative for improving digestibility for silage hybrids for decades. The improvement in ruminal intakes and digestibility is derived from reduced lignin content in Bmr mutated hybrids. Additional varieties, both naturally-occurring and transgenic, with desired traits that are useful for downstream processing as described herein are well known to those of skill in the art.

Plants useful in the present invention also include, but are not limited to, crops producing edible flowers such as cauliflower (*Brassica oleracea*), artichoke (*Cynara scolvmus*), and safflower (*Carthamus*, e.g. *tinctorius*); fruits such as apple (*Malus*, e.g. *domesticus*), banana (*Musa*, e.g. *acuminata*), berries (such as the currant, *Ribes*, e.g. *rubrum*), cherries (such as the sweet cherry, *Prunus*, e.g. *avium*), cucumber (*Cucumis*, e.g. *sativus*), grape (*Vitis*, e.g. *vinifera*), lemon (*Citrus limon*), melon (*Cucumis melo*), nuts (such as the walnut, *Juglans*, e.g. *regia*; peanut, *Arachis hypoaeae*), orange (*Citrus*, e.g. *maxima*), peach (*Prunus*, e.g. *persica*), pear (*Pyra*, e.g. *communis*), pepper (*Solanum*, e.g. *capsicum*), plum (*Prunus*, e.g. *domestica*), strawberry (*Fragaria*, e.g. *moschata*), tomato (*Lycopersicon*, e.g. *esculentum*); leafs, such as alfalfa (*Medicago*, e.g. *sativa*), sugar cane (*Saccharum*), cabbages (such as *Brassica oleracea*), endive (*Cichoreum*, e.g. *endivia*), leek (*Allium*, e.g. *porrum*), lettuce (*Lactuca*, e.g. *sativa*), spinach (*Spinacia* e.g. *oleraceae*), tobacco (*Nicotiana*, e.g. *tabacum*); roots, such as arrowroot (*Maranta*, e.g. *arundinacea*), beet (*Beta*, e.g. *vulgaris*), carrot (*Daucus*, e.g. *carota*), cassava (*Manihot*, e.g. *esculenta*), turnip (*Brassica*, e.g. *rapa*), radish (*Raphanus*, e.g. *sativus*) yam (*Dioscorea*, e.g. *esculenta*), sweet potato (*Ipomoea batatas*); seeds, such as bean (*Phaseolus*, e.g. *vulgaris*), pea (*Pisum*, e.g. *sativum*), soybean (*Glycine*, e.g. *max*), wheat (*Triticum*, e.g. *aestivum*), barley (*Hordeum*, e.g. *vulgare*), corn (*Zea*, e.g.

*mays*), rice (*Oryza*, e.g. *sativa*); grasses, such as *Miscanthus* grass (*Miscanthus*, e.g., *giganteus*) and switchgrass (*Panicum*, e.g. *virgatum*); trees such as poplar (*Populus*, e.g. *tremula*), pine (*Pinus*); shrubs, such as cotton (e.g., *Gossypium hirsutum*); and tubers, such as kohlrabi (*Brassica*, e.g. *oleraceae*), potato (*Solanum*, e.g. *tuberosum*), and the like.

G. Methods for Optimizing Ratio of Crops

The existing process of providing the optimized blend of trait-containing crop and standard crop (e.g., non trait-containing) is based upon physical blending at the point of entry into the process, such as a grain producer's facility, grain elevator or processing facility. This process requires extra capital in the form of extra grain storage and mixing equipment. In some processes, the feedstock must be uniform and homogenous. Using the current invention, the resulting crop from such an invention will result in uniform, homogenous grain containing the prescribed amount of one or more primary traits of interest.

Other methods rely upon male sterility in the standard crop in order to create controlled pollination in the crop production field. This case requires that 100% of the harvested crop contain the trait. When this controlled pollination does not occur due to drought or other factors, the required level of the primary trait of interest (such as grain oil or protein) is not achieved. In the current invention, the resulting crop does not require 100% trait-positive plant material. Rather, it is only necessary for the crop to contain an amount of trait-positive plant material that is sufficient for the downstream use. For example, for fermentation purposes, it is beneficial to utilize crop expressing one or more cellulase enzymes. However, a sufficient amount of cellulase enzyme may be provided in the fermentation process by less than 100% cellulase-expressing plant material. For example, a sufficient amount of cellulase enzyme may be provided to the fermentation process when only about 0.1% of the crop expresses cellulase, or only about 1%, about 5%, about 10%, about 20%, about 25%, about 30%, about 35%, about 40%, about 50%, about 60%, about 65%, about 70%, about 80%, about 90%, about 95%, or about 99% of the crop.

When more than one primary trait of interest is desirable in a crop useful for downstream purposes, it may be desirable to provide plant material exhibiting each of the desired traits. However, in some instances, it may be difficult to achieve the target level of expression of each gene associated with the traits of interest in the same plant. Where the target level cannot be achieved in a single variety, multiple varieties, each exhibiting one or more trait(s) of interest, can be combined at a target ratio necessary to achieve the target level of each of the primary traits of interest necessary for the downstream use.

The target level of each primary trait of interest is calculated based on the downstream use and takes into account a variety of factors including, but not limited to, plant yield, the level or expression of the primary trait of interest in an individual plant or plant part, the type of plant utilized, growth conditions for the plants, and processes involved in converting the harvested plant material to a useful product (e.g., food, feed, industrial alcohol, biofuel, fermentation product, etc.).

Thus, in some embodiments, seed for two or more varieties is blended at a ratio that results in the minimum (e.g., target) level of trait in the harvested plant material that is necessary for a downstream application. It is envisioned that one or more of the trait(s) of interest may actually be present in the harvested plant material at a higher than target level under certain growth conditions. The minimum level can be calculated by planting each variety in the blend under different of growth conditions (climate, geographic location, etc) and measuring the level of trait obtained under each condition.

In other embodiments, a customized blend suitable for growth under specific conditions can be developed. To develop a customized blend for a particular downstream use, factors affecting the level of trait in the harvested plant material (discussed supra) must be considered in the development and optimization stages to achieve a commercially useful product.

In the first stage of this process to develop a customized seed blend, the seed provider must engage in discussions with one or more entities ("collaborators") involved in the development of the customized blend. These entities may include a user of the seed blend (for example, a farmer) or a user of the harvested crop (i.e., an "end user," for example, a commercial entity), or both, but will primarily be the end user.

The collaborator(s) must define the downstream use and provide information pertaining to the manufacturing processes required to convert the crop to the intended downstream product. For example, an ethanol production facility interested in developing a customized blend for fermentation feedstock would provide information related to the chemical conversion and/or fermentation processes involved in converting the crop to ethanol, including the reaction conditions and materials required for each step in the conversion. A general formulation of trait necessary in the downstream processes is developed at this stage. For ethanol production, it may be determined that an optimal combination of certain cellulase enzymes is desirable in the crop. Other logistical factors, such as growth conditions of the plants and crop flow patterns of the grower and/or distributor of the crop, will be discussed and considered at this stage.

The next stage involves laboratory development and testing. Laboratory development may include, for example, developing new plants exhibiting the trait(s) of interest, determining various molecular and/or biochemical properties of these plants or enzymes/nucleic acids expressed in these plants (including relative expression level in the plants as well as activity of the trait or trait-containing plant in downstream processes), optimizing enzymes or nucleic acids for use in these plants, establishing a broad range of dosing feasible to achieve the target level of each trait in the crop. The "target level" or "predetermined level" is the level of trait necessary in the crop for the intended downstream use.

Following laboratory testing, pilot scale trialing is used for proof of concept and to narrow the range and optimize the target level for each trait of interest as well as the conditions for growth and for the downstream processes. By "proof of concept" is intended that the crop harvested from plants grown from the customized seed blend is sufficient for the intended downstream use. The amount of seed required to produce a crop containing the target level of a primary trait of interest is calculated as a proportion of the total plant material (both trait-containing and non-trait containing) necessary for the intended downstream use. For example, if an ethanol producer wishes to use 1 ton of crop for ethanol conversion, the amount of trait-containing crop necessary for this conversion will be less than 100% of the total crop. The amount of seed necessary to produce this percentage of crop is referred to herein as the "predetermined ratio" or "target ratio."

At this stage, it is possible to begin defining value points for the use of the customized seed blend, such as cost savings to the end user that result from utilizing an optimized blend for the intended downstream use. The value points can be related, for example, to the efficiency of the process due to the combination of traits in the crop (including the trait itself and/or the level of trait utilized) or decreased costs involved in utilizing a crop containing less than 100% trait-positive plants. For the seed producer, it is possible to assess capital investment necessary to provide the customized blend, which can be used to develop appropriate fee structures and profit margins for the service.

Commercial scale trialing in which full production scale is run for a limited period of time is then utilized to validate the target level of trait(s) necessary for the customized blend. Further refinements to the conditions related to growth and/or processing may also be made at this stage. It will be necessary to coordinate crop supply, storage, and transportation, as well as other manufacturing and logistical factors necessary for full commercial utilization of the customized blend. The variables realized from this process (such as target level, target ratio, value points, etc.) can be used to develop customized blends for other end users, or for other downstream processes.

H. Methods of Generating Seeds Comprising Trait(s) of Interest

Plants exhibiting primary and secondary traits of interest, in combination with other characteristics important for production and quality, can be incorporated into plant lines through breeding or through common genetic engineering technologies. Breeding approaches and techniques are known in the art. See, for example, Welsh J. R., Fundamentals of Plant Genetics and Breeding, John Wiley & Sons, NY (1981); Crop Breeding, Wood D. R. (Ed.) American Society of Agronomy Madison, Wis. (1983); Mayo O., The Theory of Plant Breeding, Second Edition, Clarendon Press, Oxford (1987); Singh, D. P., Breeding for Resistance to Diseases and Insect Pests, Springer-Verlag, NY (1986); and Wricke and Weber, Quantitative Genetics and Selection Plant Breeding, Walter de Gruyter and Co., Berlin (1986).

The relevant techniques are well known in the art and include but are not limited to hybridization, inbreeding, backcross breeding, multi-line breeding, dihaploid inbreeding, variety blend, interspecific hybridization, aneuploid techniques, etc. Hybridization techniques also include the sterilization of plants to yield male or female sterile plants by mechanical, genetic (including transgenic), chemical, or biochemical means.

In some embodiments, it may be necessary to genetically modify plants to obtain a trait of interest using routine methods of plant engineering. In this example, one or more nucleic acid sequences associated with the trait of interest can be introduced into the plant. The plants can be homozygous or heterozygous for the nucleic acid sequence(s). Expression of this sequence (either transcription and/or translation) results in a plant exhibiting the trait of interest. Expression of this heterologous nucleic acid sequence may result in enhancement or inhibition of the activity of an endogenous gene or protein, or may confer a new property to the plant. Methods for enhancing or inhibiting the activity of a target gene or protein are well known in the art.

To obtain a plant exhibiting a particular trait of interest, it may be necessary to inhibit or enhance the expression or activity of an endogenous gene in that plant. The terms "inhibit," "inhibition," and "inhibiting" as used herein refer to any decrease in the expression or function of a target gene product, including any relative decrement in expression or function up to and including complete abrogation of expression or function of the target gene product. Likewise, the terms "enhancing" or "increasing" as used herein refer to any increase in the expression or function of a target gene product, including any relative increment in expression or function of the target gene product. The term "expression" as used herein in the context of a gene product refers to the biosynthesis of that gene product, including the transcription and/or translation and/or assembly of the gene product. Inhibition or enhancement of expression or function of a target gene product (i.e., a gene product of interest) can be in the context of a comparison between any two plants, for example, expression or function of a target gene product in a genetically altered plant versus the expression or function of that target gene product in a corresponding wild-type plant. Alternatively, inhibition of expression or function of the target gene product can be in the context of a comparison between plant cells, organelles, organs, tissues, or plant parts within the same plant or between plants, and includes comparisons between developmental or temporal stages within the same plant or between plants.

Plant Expression Cassettes

A plant variety exhibiting a trait of interest can be obtained by introducing into the plant a nucleic acid sequence associated with a trait of interest. The nucleic acid sequences may be present in DNA constructs or expression cassettes. "Expression cassette" as used herein means a nucleic acid molecule capable of directing expression of a particular nucleotide sequence in an appropriate host cell, comprising a promoter operatively linked to the nucleotide sequence of interest (i.e., a nucleic acid sequence associated with a trait of interest, or a nucleic acid sequence capable of inhibiting the function of a target protein, where inhibition is associated with the trait of interest) which is operatively linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. Additionally, the promoter can also be specific to a particular tissue or organ or stage of development.

The expression cassette may optionally comprise a transcriptional and translational termination region (i.e. termination region) functional in plants. In some embodiments, the expression cassette comprises a selectable marker gene to allow for selection for stable transformants. Expression constructs of the invention may also comprise a leader sequence and/or a sequence allowing for inducible expression of the polynucleotide of interest. See, Guo et al. (2003) Plant J. 34:383-92 and Chen et al. (2003) Plant J. 36:731-40 for examples of sequences allowing for inducible expression.

The regulatory sequences of the expression construct are operably linked to the nucleic acid sequence of interest. By "operably linked" is intended a functional linkage between a promoter and a second sequence wherein the promoter sequence initiates and mediates transcription of the DNA sequence corresponding to the second sequence. Generally, operably linked means that the nucleotide sequences being linked are contiguous.

Any promoter capable of driving expression in the plant of interest may be used in the practice of the invention. The promoter may be native or analogous or foreign or heterologous to the plant host. The terms "heterologous" and "exogenous" when used herein to refer to a nucleic acid sequence (e.g. a DNA or RNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" nucleic acid (e.g. DNA) sequence is a nucleic acid (e.g. DNA or RNA) sequence naturally associated with a host cell into which it is introduced. The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to that sequence.

Some suitable promoters initiate transcription only, or predominantly, in certain cell types. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano, et al., Plant Cell, 1:855-866 (1989); Bustos, et al., Plant Cell, 1:839-854 (1989); Green, et al., EMBO J. 7, 4035-4044 (1988); Meier, et al., Plant Cell, 3, 309-316 (1991); and Zhang, et al., Plant Physiology 110: 1069-1079 (1996).

Promoters active in photosynthetic tissue in order to drive transcription in green tissues such as leaves and stems are also encompassed by the present invention. Most suitable are promoters that drive expression only or predominantly in such tissues. The promoter may confer expression constitutively throughout the plant, or differentially with respect to the green tissues, or differentially with respect to the developmental stage of the green tissue in which expression occurs, or in response to external stimuli.

Examples of such promoters include the ribulose-1,5-bisphosphate carboxylase (RbcS) promoters such as the RbcS promoter from eastern larch (*Larix laricina*), the pine cab6 promoter (Yamamoto et al. (1994) Plant Cell Physiol. 35:773-778), the Cab-1 gene promoter from wheat (Fejes et al. (1990) Plant Mol. Biol. 15:921-932), the CAB-1 promoter from spinach (Lubberstedt et al. (1994) Plant Physiol. 104:997-1006), the cab1R promoter from rice (Luan et al. (1992) Plant Cell 4:971-981), the pyruvate orthophosphate dikinase (PPDK) promoter from corn (Matsuoka et al. (1993) Proc Natl Acad Sci USA 90:9586-9590), the tobacco Lhcb1*2 promoter (Cerdan et al. (1997) Plant Mol. Biol. 33:245-255), the *Arabidopsis thaliana* SUC2 sucrose-H+ symporter promoter (Truernit et al. (1995) Planta 196:564-570), and thylakoid membrane protein promoters from spinach (psaD, psaF, psaE, PC, FNR, atpC, atpD, cab, rbcS. Other promoters that drive transcription in stems, leafs and green tissue are described in U.S. Patent Publication No. 2007/0006346, herein incorporated by reference in its entirety.

In some other embodiments of the present invention, inducible promoters may be desired. Inducible promoters drive transcription in response to external stimuli such as chemical agents or environmental stimuli. For example, inducible promoters can confer transcription in response to hormones such as giberellic acid or ethylene, or in response to light or drought.

A variety of transcriptional terminators are available for use in expression cassettes. These are responsible for the termination of transcription beyond the transgene and correct mRNA polyadenylation. The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Appropriate transcriptional terminators are those that are known to function in plants and include the CAMV 35S terminator, the tml terminator, the nopaline synthase terminator and the pea rbcs E9 terminator. These can be used in both monocotyledons and dicotyledons. In addition, a gene's native transcription terminator may be used.

Generally, the expression cassette will comprise a selectable marker gene for the selection of transformed cells. Selectable marker genes are utilized for the selection of transformed cells or tissues.

Numerous sequences have been found to enhance gene expression from within the transcriptional unit and these sequences can be used in conjunction with the genes of this invention to increase their expression in transgenic plants.

Various intron sequences have been shown to enhance expression. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop. 1: 1183-1200 (1987)). In the same experimental system, the intron from the maize bronze 1 gene had a similar effect in enhancing expression. Intron sequences have been routinely incorporated into plant transformation vectors, typically within the non-translated leader.

A number of non-translated leader sequences derived from viruses are also known to enhance expression. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693-8711 (1987); Skuzeski et al. Plant Molec. Biol. 15: 65-79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. PNAS USA 86:6126-6130 (1989)); potyvirus leaders, for example, TEV leader (Tobacco Etch Virus) (Allison et al., 1986); MDMV leader (Maize Dwarf Mosaic Virus); Virology 154: 9-20); human immunoglobulin heavy-chain binding protein (BiP) leader, (Macejak, D. G., and Samow, P., Nature 353: 90-94 (1991); untranslated leader from the coat protein mRNA of alfalfa mosaic virus (AMV RNA 4), (Jobling, S. A., and Gehrke, L., Nature 325:622-625 (1987); tobacco mosaic virus leader (TMV), (Gallie, D. R. et al., Molecular Biology of RNA, pages 237-256 (1989); and Maize Chlorotic Mottle Virus leader (MCMV) (Lommel, S. A. et al., Virology 81:382-385 (1991). See also, Della-Cioppa et al., Plant Physiology 84:965-968 (1987).

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104-15109 (1988)). These signal sequences can be fused to heterologous gene products to effect the import of heterologous products into the chloroplast (van den Broeck, et al. Nature 313: 358-363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

In order to ensure the localization in the plastids it is conceivable to use one of the following transit peptides: of the plastidic Ferredoxin: NADP+ oxidoreductase (FNR) of spinach which is enclosed in Jansen et al. (Current Genetics 13 (1988), 517-522). In particular, the sequence ranging from the nucleotides-171 to 165 of the cDNA sequence disclosed therein can be used, which comprises the 5' non-translated region as well as the sequence encoding the transit peptide. Another example is the transit peptide of the waxy protein of maize including the first 34 amino acid residues of the mature waxy protein (Klosgen et al., Mol. Gen. Genet. 217 (1989), 155-161). It is also possible to use this transit peptide without the first 34 amino acids of the mature protein. Furthermore, the signal peptides of the ribulose bisposphate carboxylase small subunit (Wolter et al., Proc. Natl. Acad. Sci. USA 85 (1988), 846-850; Nawrath et al., Proc. Natl. Acad. Sci. USA 91 (1994), 12760-12764), of the NADP malat dehydrogenase (Galiardo et al., Planta 197 (1995), 324-332), of the glutathione reductase (Creissen et al., Plant J. 8 (1995), 167-175) or of the R1 protein Lorberth et al. (Nature Biotechnology 16, (1998), 473-477) can be used.

Plant Transformation

Once a nucleic acid sequence associated with a primary or secondary trait of interest has been cloned into an expression system, it is transformed into a plant cell. The receptor and target expression cassettes of the present invention can be introduced into the plant cell in a number of art-recognized ways. The term "introducing" in the context of a polynucleotide, for example, a nucleotide construct of interest, is intended to mean presenting to the plant the polynucleotide in such a manner that the polynucleotide gains access to the interior of a cell of the plant. Where more than one polynucleotide is to be introduced, these polynucleotides can be assembled as part of a single nucleotide construct, or as separate nucleotide constructs, and can be located on the same or different transformation vectors.

Accordingly, these polynucleotides can be introduced into the host cell of interest in a single transformation event, in separate transformation events, or, for example, in plants, as part of a breeding protocol. The methods of the invention do not depend on a particular method for introducing one or more polynucleotides into a plant, only that the polynucleotide(s) gains access to the interior of at least one cell of the plant. Methods for introducing polynucleotides into plants are known in the art including, but not limited to, transient transformation methods, stable transformation methods, and virus-mediated methods.

"Transient transformation" in the context of a polynucleotide is intended to mean that a polynucleotide is introduced into the plant and does not integrate into the genome of the plant.

By "stably introducing" or "stably introduced" in the context of a polynucleotide introduced into a plant is intended the introduced polynucleotide is stably incorporated into the plant genome, and thus the plant is stably transformed with the polynucleotide.

"Stable transformation" or "stably transformed" is intended to mean that a polynucleotide, for example, a nucleotide construct described herein, introduced into a plant integrates into the genome of the plant and is capable of being inherited by the progeny thereof, more particularly, by the progeny of multiple successive generations.

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the npt11 gene, which confers resistance to kanamycin and related antibiotics (Messing & Vierra. Gene 19: 259-268 (1982); Bevan et al., Nature 304:184-187 (1983)), the bar gene, which confers resistance to the herbicide phosphinothricin (White et al., Nucl. Acids Res 18: 1062 (1990), Spencer et al. Theor. Appl. Genet. 79: 625-631 (1990)), the hph or aph4 gene, which confers resistance to the antibiotic hygromycin (Blochinger & Diggelmann, Mol Cell Biol 4: 2929-2931), and the dhfr gene, which confers resistance to methatrexate (Bourouis et al., EMBO J. 2(7): 1099-1104 (1983)), the EPSPS gene, which confers resistance to glyphosate (U.S. Pat. Nos. 4,940,935 and 5,188,642), and the mannose-6-phosphate isomerase gene, which provides the ability to metabolize mannose (U.S. Pat. Nos. 5,767,378 and 5,994,629).

Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

Many vectors are available for transformation using *Agrobacterium tumefaciens*. These typically carry at least one T-DNA border sequence and include vectors such as pBIN19 (Bevan, Nucl. Acids Res. (1984)). For the construction of vectors useful in *Agrobacterium* transformation, see, for example, US Patent Application Publication No. 2006/0260011, herein incorporated by reference.

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the preferred selection for the species being transformed. For the construction of such vectors, see, for example, US Application No. 20060260011, herein incorporated by reference.

For expression of a nucleotide sequence useful in the present invention in plant plastids, plastid transformation vector pPH143 (WO 97/32011, example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J. 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. Plant Cell 5: 159-169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Hofgen & Willmitzer, Nucl. Acids Res. 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both of these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093-1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (*Plant Cell* 2: 603-618 (1990)) and Fromm et al. (*Biotechnology* 8: 833-839 (1990)) have published techniques for transformation of A188-derived maize line using particle bombardment. Furthermore, WO 93/07278 and Koziel et al. (*Biotechnology* 11: 194-200 (1993)) describe techniques for the transformation of elite inbred lines of maize by particle bombardment. This technique utilizes immature maize embryos of 1.5-2.5 mm length excised from a maize ear 14-15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep 7: 379-384 (1988); Shimamoto et al. Nature 338: 274-277 (1989); Datta et al. Biotechnology 8: 736-740 (1990)). Both types are also routinely transformable using particle bombardment (Christou et al. Biotechnology 9: 957-962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of *Dactylis* and wheat. Furthermore, wheat transformation has been described by Vasil et al. (Biotechnology 10: 667-674 (1992)) using particle bombardment into cells of type C long-term regenerable callus, and also by Vasil et al. (Biotechnology 11:1553-1558 (1993)) and Weeks et al. (Plant Physiol. 102: 1077-1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashiga & Skoog, Physiologia Plantarum 15: 473-497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 hours and are then bombarded. Twenty embryos per target plate is typical, although not critical. An appropriate gene-carrying plasmid (such as pCIB3064 or pSOG35) is precipitated onto micrometer size gold particles using standard procedures. Each plate of embryos is shot with the DuPont BIOLISTICS® helium device using a burst pressure of about 1000 psi using a standard 80 mesh screen. After bombardment, the embryos are placed back into the dark to recover for about 24 hours (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described. See, WO 94/00977 and U.S. Pat. No. 5,591,616, each of which is incorporated herein by reference. See also, Negrotto et al., Plant Cell Reports 19: 798-803 (2000), incorporated herein by reference.

For example, rice (*Oryza sativa*) can be used for generating transgenic plants. Various rice cultivars can be used (Hiei et al., 1994, Plant Journal 6:271-282; Dong et al., 1996, Molecular Breeding 2:267-276; Hiei et al., 1997, Plant Molecular Biology, 35:205-218). Also, the various media constituents described below may be either varied in quantity or substituted. Embryogenic responses are initiated and/or cultures are established from mature embryos by culturing on MS-CIM medium (MS basal salts, 4.3 g/liter; B5 vitamins (200×), 5 ml/liter; Sucrose, 30 g/liter; proline, 500 mg/liter; glutamine, 500 mg/liter; casein hydrolysate, 300 mg/liter; 2,4-D (1 mg/ml), 2 ml/liter; adjust pH to 5.8 with 1 N KOH; Phytagel, 3 g/liter). Either mature embryos at the initial stages of culture response or established culture lines are inoculated and co-cultivated with the *Agrobacterium tumefaciens* strain LBA4404 (*Agrobacterium*) containing the desired vector construction. *Agrobacterium* is cultured from glycerol stocks on solid YPC medium (100 mg/L spectinomycin and any other appropriate antibiotic) for about 2 days at 28° C. *Agrobacterium* is re-suspended in liquid MS-CIM medium. The *Agrobacterium* culture is diluted to an OD600 of 0.2-0.3 and acetosyringone is added to a final concentration of 200 uM. Acetosyringone is added before mixing the solution with the rice cultures to induce *Agrobacterium* for DNA transfer to the plant cells. For inoculation, the plant cultures are immersed in the bacterial suspension. The liquid bacterial suspension is removed and the inoculated cultures are placed on co-cultivation medium and incubated at 22° C. for two days. The cultures are then transferred to MS-CIM medium with Ticarcillin (400 mg/liter) to inhibit the growth of *Agrobacterium*. For constructs utilizing the PMI selectable marker gene (Reed et al., In Vitro Cell. Dev. Biol.-Plant 37:127-132), cultures are transferred to selection medium containing Mannose as a carbohydrate source (MS with 2% Mannose, 300 mg/liter Ticarcillin) after 7 days, and cultured for 3-4 weeks in the dark. Resistant colonies are then transferred to regeneration induction medium (MS with no 2,4-D, 0.5 mg/liter IAA, 1 mg/liter zeatin, 200 mg/liter timentin 2% Mannose and 3% Sorbitol) and grown in the dark for 14 days. Proliferating colonies are then transferred to another round of regeneration induction media and moved to the light growth room. Regenerated shoots are transferred to GA7 containers with GA7-1 medium (MS with no hormones and 2% Sorbitol) for 2 weeks and then moved to the greenhouse when they are large enough and have adequate roots. Plants are transplanted to soil in the greenhouse (to generation) grown to maturity, and the $T_1$ seed is harvested.

For the transformation of plastids, seeds of *Nicotiana tabacum* c.v. "Xanthienc" are germinated seven per plate in a 1" circular array on T agar medium and bombarded 12-14 days after sowing with 1 um tungsten particles (M10, Biorad, Hercules, Calif.) coated with DNA from plasmids pPH143 and pPH145 essentially as described (Svab, Z. and Maliga, P. (1993) PNAS 90, 913-917). Bombarded seedlings are incubated on T medium for two days after which leaves are excised and placed abaxial side up in bright light (350-500 umol photons/$m^2$/s) on plates of RMOP medium (Svab, Z., Hajdukiewicz, P. and Maliga, P. (1990) PNAS 87, 8526-8530) containing 500 ug/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) Molecular Cloning: A Laboratory Manual, Cold Spring Harbor Laboratory, Cold Spring Harbor). BamHI/EcoRI-digested total cellular DNA (Mettler, I. J. (1987) Plant Mol Biol Reporter 5, 346349) is separated on 1% Tris-borate (TBE) agarose gels, transferred to nylon membranes (Amersham) and probed with .sup.32P-labeled random primed DNA sequences corresponding to a 0.7 kb BamHI/HindIII DNA fragment from pC8 containing a portion of the rps 7/12 plastid targeting sequence. Homoplasmic shoots are rooted aseptically on spectinomycin-containing MS/IBA medium (McBride, K. E. et al. (1994) PNAS 91, 7301-7305) and transferred to the greenhouse.

The plants obtained via transformation with a nucleic acid sequence of the present invention can be any of a wide variety of plant species, including those of monocots and dicots; however, the plants used in the method of the invention are preferably selected from the list of agronomically important target crops set forth supra. The expression of a gene of the present invention in combination with other characteristics important for production and quality can be incorporated into plant lines through breeding. Breeding approaches and techniques are known in the art. See, for example, Welsh J. R., Fundamentals of Plant Genetics and Breeding, John Wiley & Sons, NY (1981); Crop Breeding, Wood D. R. (Ed.) American Society of Agronomy Madison, Wis. (1983); Mayo O., The Theory of Plant Breeding, Second Edition, Clarendon Press, Oxford (1987); Singh, D. P., Breeding for Resistance to Diseases and Insect Pests, Springer-Verlag, NY (1986); and Wricke and Weber, Quantitative Genetics and Selection Plant Breeding, Walter de Gruyter and Co., Berlin (1986).

The genetic properties engineered into the transgenic seeds and plants described above are passed on by sexual reproduction or vegetative growth and can thus be maintained and propagated in progeny plants. Generally, maintenance and propagation make use of known agricultural methods developed to fit specific purposes such as tilling, sowing or harvesting.

The following examples are offered by way of illustration and not by way of limitation.

EXPERIMENTAL

Example 1

Glucose Production Using Amylase- and Glucoamylase-Expressing Plants

Two different types of corn were ground to a flour and mixed at set ratios. The first type was the 797GL3 amylase corn (i.e., "Corn Amylase", or "CA"; described in U.S. Patent Application No. 2006/0230473, filed Oct. 12, 2006, herein incorporated by reference) from event 3272. The second was corn that expresses the *Thermomyces lanuginosus* glucoamylase enzyme (i.e., "TlGA"). This corn was transformed with construct pNOV12493, which has the gamma-zein promoter driving the TlGA gene. The enzyme was targeted to the apoplast of endosperm cells.

Figure 2:
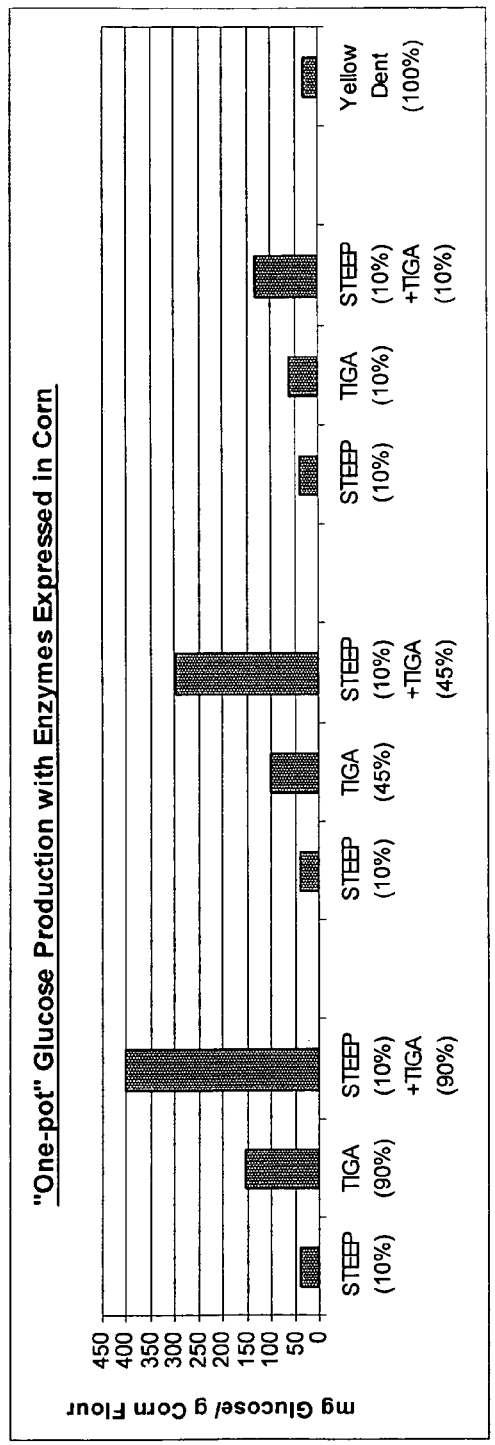
FIG. 2 demonstrates the synergy between CA (referred to as STEEP) and TlGA. The incubations were performed for 2 h at 70° C.

The transgenic corn flours were mixed at different ratios (19:1, 9:1, 5:1, 4:1, and 1:1; TlGA:CA, w/w) in water, incubated at different temperatures (30-90° C.) for varying times (1 h-72 h), and at varying solids level (1%, 10%, and 25% total solids, w/v). The balance of solids in the blend consisted of yellow dent corn flour. The results were compared to a 100% composition of yellow dent corn flour. Glucose production was measured and used to calculate the percentage of starch hydrolyzed. FIG. 2 demonstrates the synergy between glucoamylase (TlGA) and amylase (STEEP) for glucose production.

Example 2

Optimization of GA and CA Blend

Figure 3:
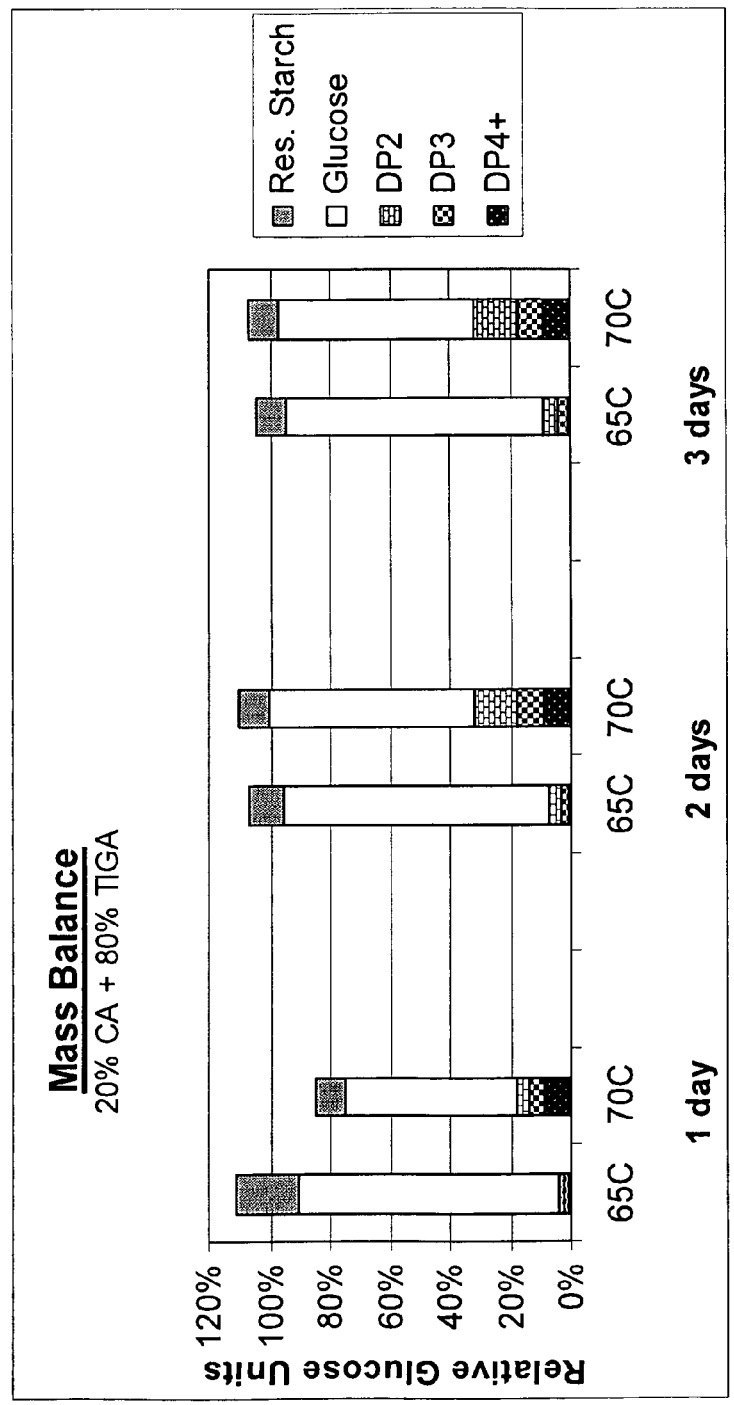
FIG. 3 shows the results of the mass balance experiment. An admix of 80% TlGA flour and 20% CA flour was incubated at 65° C. or 70° C. for 3 days. Samples were taken each day, and soluble sugars and residual starch were measured in each sample.

Additional work (not shown) was done to optimize the conditions to maximize starch conversion to glucose. The optimum temperature for this assay was 65-70° C. The optimum admix was 4:1 (80% TlGA corn and 20% Corn Amylase) in a 10% solids mixture (10% TIGA/CA blend, 90% yellow dent corn). By incubating the admix for 1-3 days, greater than 90% of the starch is converted to glucose and small soluble sugars (FIG. 3). There is a temperature dependence for the balance between glucose and small soluble sugars.

By incubating an 80% mix of *Thermomyces lanuginosus* glucoamylase-expressing corn flour with 20% of 797GL3 amylase-expressing corn flour at 65-70° C., we were able to degrade >90% of the starch to glucose and other soluble sugars. Because this process was looking at a "one pot" starch to glucose conversion, it was not optimized for the Corn Amylase modified conventional ethanol process. By doing so, it is expected that even more of the starch can be hydrolyzed. Also, these admixes are specific to the TlGA events that were tested and can be used as a model to optimize blends for specific applications using other trait-containing crops.

This combination of amylase and glucoamylase expressed in corn shows the ability to digest the starch to fermentable sugars, therefore, it should work well in an ethanol fermentation process. Furthermore, a bag blend of the 2 events of enzyme-containing corn has the ability to deliver the correct mix of harvested plant material to the ethanol production facility.

Example 3

Pre-Planting Determination of Amylase and Glucoamylase Activity in Harvested Grain Admixes The amylase activity in harvested grain can be determined from the yield potential of corn varieties comprising the seed admix, the expression level of the trait in the corn variety, and the ratio in which the corn varieties are blended in the seed admix. The yield potential (Y) in weight unit per surface unit [e.g. bushels per acre (bu/ac)] for trait expressing corn varieties can be determined by methods well described in the art. The level of enzyme expression in plants (X) in activity unit per mass unit [e.g. activity units per bushel (U/bu)] can be determined by quantitative assay methods described below. The percentages (Z) of the corn seed of the trait expressing corn variety and seed of non-trait corn variety are determined by weighing both varieties prior to seed blending. The amylase activity [E(A)] in harvested grain in activity units per mass unit (e.g. U/bushel) can be calculated by the equation below:

$$E(A)=(X_A \times Z_A \times Y_A)/[(Z_A \times Y_A)+(Z_0 \times Y_0)] \qquad \text{Equation 1}$$

Where:
E(A) is the amylase activity level in harvested grain
$X_A$ is the expression level of amylase in grain
$Y_A$ is the yield potential of the amylase expressing corn variety
$Z_A$ is the percentage of trait expressing corn variety
$Y_0$ is the yield potential of the non-trait corn variety
$Z_0$ is the percentage of non-trait corn variety The amylase activity E(A) and glucoamylase activity E(G) in harvested grain stemming from an amylase and glucoamylase seed admix in activity units per mass unit (U/bushel) can be calculated by equation 2A (amylase) and 2B (glucoamylase) below:

$$E(A)=\{(X_A \times Z_A \times Y_A)/[(Z_A \times Y_A)+(Z_G \times Y_G)+(Z_0 \times Y_0)]\} \qquad \text{Equation 2A}$$

$$E(G)=\{(X_G \times Z_G \times Y_G)/[(Z_A \times Y_A)+(Z_G \times Y_G)+(Z_0 \times Y_0)]\} \qquad \text{Equation 2B}$$

Where:
E(A) is the amylase activity level in harvested grain
E(G) is the glucoamylase activity level in harvested grain
$X_A$ is the amylase expression level in grain
$Y_A$ is the yield potential of the amylase expressing corn variety
$Z_A$ is the percentage of amylase-expressing corn variety
$X_G$ is the glucoamylase expression level in grain
$Y_G$ is the yield potential of the glucoamylase-expressing corn variety
$Z_G$ is the percentage of glucoamylase expressing corn variety
$Y_0$ is the yield potential of the non-trait corn variety
$Z_0$ is the percentage of non-trait corn variety Example 4

Pre-Harvest Amylase Determination of Admix Ratio

An appropriate number of plants in field is sampled prior to harvest and tested for the presence of gene encoding enzyme. The number of sampled plants is proportional to the desired admix ratio. E.g., 200 plants are sampled for 10% admix and 400 plants for 5% admix. The ratio of plants with and without enzyme coding sequence (+/−ratio) is determined by PCR methods detecting the enzyme coding sequence (Lipp et al. (2005) *J. of AOAC International* Vol. 88 (1) 136).

Example 5

Post-Harvest Enzyme Assay I

An appropriately sized grain sample is ground to fine flour. The enzyme is extracted from sub-samples of flour by addition of extraction buffer and vigorous shaking at elevated temperature. The extract is centrifuged and the supernatant is collected. The supernatant is tested for its ability to convert starch into oligosaccharides. An appropriate amount of supernatant is mixed with assay buffer and calorimetric substrate. The mixture is incubated at 60° C. for 30 minutes. Formation of colored product indicative of amylase activity on calorimetric substrate is measured by visible light spectrometry. This assay is repeated appropriately to represent to the storage unit (bin or silo).

Example 6

Post-Harvest Enzyme Assay II

Lateral flow detection devices (aka. dipsticks) are customized to visualize a pre-set amount of enzyme. I.e. a desired admix ratio (e.g. 25%) is converted in mass units (e.g. microgram) of enzyme based on known desired expression level. The limit of detection of the detection device is set to be the enzyme level corresponding to the desired admix ratio. An appropriate grain sample is ground to fine flour. The enzyme is extracted from the flour by addition of extraction buffer and vigorous shaking at elevated temperature. The lateral flow detection device is inserted and developed by described methodology (Ahmed (2002) *Trends Biotechnol* Vol. 20 (5), 215). A positive test is indicative of presence of enzyme level corresponding to desired admix ratio or higher.

Example 7

Bag Blend Produced by Field Blending of Seed

A grain producer desires to produce a grain crop containing 15% of the maximum possible enzyme expression (determined from 100% hemizygous grain) for sale to a bioprocessing facility for use as their fermentation feedstock. The seed that the grain producer will plant has been blended prior to packaging. The seed blend is constructed by the seed producer and may contain near-isogenic hybrids or hybrids of different genotype with synchronous flowering. The seed production field utilizes a common pollen parent and the female parent blocks are planted to either 100% enzyme or 100% non-enzyme containing genotype in the 15:85 ratios, cumulatively across the seed field. The ratio assumes a similar yield potential among each variety in the blend. Where the yield potential is different, the equation in Example 3 can be used to calculate the appropriate ratio.

The hybrid seed produced on the female parent is harvested without respect to enzyme content. The seed is blended as it is harvested and brought in to the processing and drying facility is 15:85 blended. (This is common practice for using male sterile female parent, however the blend is usually 80:20 sterile:fertile genotype). Conditioning and processing of the resulting seed blend continues as is well known in the art. The 15:85 blended seed is planted in bulk (not segregated by genotype) by the grain producer and the resulting plants allowed to open pollinate. The resulting grain is harvested in bulk and delivered as such to the bioprocessing facility.

Example 8

Bag Blend Produced by Planting Segregated Seed

A grain producer desires to produce a grain crop containing 25% of the maximum possible enzyme expression (determined from 100% hemizygous grain) for sale to the bioprocessing facility for use as their fermentation feedstock. The seed that the grain producer will plant is blended in the planter suitable for delivering different genotypes in each row planted. The grain producer is delivered seeds that are either 100% trait containing, or 0% trait containing, in each package. The grain producer will place trait containing seeds in the containers feeding 25% of the rows planted in the field and non-trait containing seeds in containers feeding the remaining 75% of the rows planted. For example, a grain producer uses a 16-row planter with individual seed boxes feeding each row. The producer places trait containing seed in four of the sixteen feeder boxes and non-trait containing seeds in the remaining twelve feeder boxes producing the required 25% ratio of trait-containing seeds. The grain producer plants the field maintaining this ratio. The resulting plants are allowed to open pollinate and the grain is harvested in bulk to be delivered as such to the bioprocessing facility.

Example 9

Using Seed Colorants to Distinguish Trait-Containing Seeds in the Bag Blend

In order to readily distinguish those seeds in the bag blend that contain the desired trait from those that do not, the trait-containing seeds would have a differential colorant applied to the seed coat at the time the fungicide is applied, as is well known in the art. For example, trait-containing seeds may be colored bright orange while the non-trait seeds have a blue colorant applied to them.

Example 10

Using Structural Genes Encoding Anthocyanin Expression in the Grain to Distinguish Trait-Containing Grain from Non-Trait Containing Grain in the Resulting Grain Mixture Delivered to Bioprocessing Facility In order to readily distinguish grain that contains the desired trait from grain that does not contain the resulting grain, an anthocyanin-producing structural gene is employed to visually differentiate the trait-containing grain by color. For example, a structural gene (A) is backcrossed into one, or both, parents of the hybrid cross containing the desired trait as is well known in the art. Allele "A" is dominant to allele "a" which is prevalent in corn produced in the United States. Thus any pollen, or ovule, that will result in the gene for the desired enzyme trait being expressed will also contain the "A" allele for anthocyanin production. Grain produced as a result of fertilization of ovules containing the enzyme trait will thus be colored as a result of the "A" allele being present. This cosegregation of the enzyme trait and the coloration due to the "A" allele results in the positive distinction of enzyme trait-containing grain from the uncolored, non-trait containing grain.

Example 11

Corn Phytase Bag Blend

Grain from corn expressing phytase derived from a homozygous phytase hybrid was blended with conventional corn grain at varying ratios (5%, 10%, 15%, 25%, or 100% phytase corn) and planted in four different geographic locations. Grain was harvested and aliquoted into a total of 16 1-kg samples (4 sets of samples from each of the 4 locations). For analysis of phytase activity, one sub-sample of 100 grams from each 1-kg sample was prepared for analysis by milling 100 g in a Perten Hammer mill using a 0.8 mm screen. Samples were weighed out in triplicate for extraction and assayed in triplicate using the method described in International Patent Application Publication WO 2007/002192. The results are presented in Table 1 below.

TABLE 1

Activity assay results. The average phytase unit (FTU)/g is the average of three different extractions.

| MATID | Location | Admix | Average FTU/g | Triplicate Extraction STDEV (FTU/g) | Triplicate Extraction % CV | % of homozygous phytase sample |
|---|---|---|---|---|---|---|
| 06KD000060 | 8409 | 100% homozygous phytase | 1157.8 | 18.8 | 1.6% | 100.0% |
| 07KD000000 | 8409 | 5% admix | 67.0 | 5.7 | 8.5% | 5.8% |
| 07KD000001 | 8409 | 15% admix | 75.4 | 6.4 | 8.5% | 6.5% |
| 07KD000002 | 8409 | 25% admix | 306.9 | 3.8 | 1.2% | 26.5% |
| 06KD000066 | 7630 | 100% homozygous phytase | 1347.9 | 29.1 | 2.2% | 100.0% |
| 07KD000003 | 7630 | 5% admix | 43.7 | 1.6 | 3.7% | 3.2% |
| 07KD000004 | 7630 | 15% admix | 196.8 | 1.9 | 1.0% | 14.6% |
| 07KD000005 | 7630 | 25% admix | 403.9 | 3.8 | 1.0% | 30.0% |
| 06KD000071 | 761N | 100% homozygous phytase | 1249.7 | 2.4 | 0.2% | 100.0% |
| 07KD000006 | 761N | 5% admix | 10.3 | 0.0 | 0.3% | 0.8% |
| 07KD000007 | 761N | 15% admix | 127.6 | 1.2 | 0.9% | 10.2% |
| 07KD000008 | 761N | 25% admix | 247.6 | 5.0 | 2.0% | 19.8% |
| 06KD000077 | 7334 | 100% homozygous phytase | 1450.3 | 17.6 | 1.2% | 100.0% |
| 07KD000009 | 7334 | 5% admix | 35.0 | 1.8 | 5.2% | 2.4% |
| 07KD000010 | 7334 | 15% admix | 151.3 | 5.5 | 3.6% | 10.4% |
| 07KD000011 | 7334 | 25% admix | 422.5 | 3.8 | 0.9% | 29.1% |

Example 12

Samples for Corn Amylase Bag Blend

Seeds from 4 different hemizygous Corn Amylase (CA) expressing hybrids were blended with isogenic negative seeds of each hybrid at varying ratios (5%, 15%, 25%, or 100% Corn Amylase seeds) and planted in five different geographic locations. The corn in the plots was allowed to open pollinate and 20 ears were harvested from the center of the plot for each location and each hybrid to make a composite sample of approximately 1 kg. For analysis of alpha-amylase activity, one sub-sample of 250 grams from each 1-kg sample was milled using a Perten Laboratory 3600 Disc Mill at setting 0. Commodity corn NK N58-D1 was milled using the same mill at the same setting to use as a negative control. Flour moisture content was taken by using approximately 0.75 g of flour on the Mettler Toledo HB43 Halogen Moisture Analyzer at 130° C. The moisture content was used to calculate dry weight using the formula:

(Wet weight)=(dry weight)/(1−(% flour moisture/100))

Standard Curve for Predicting Admix Ratio:

Flour from 100% CA grain was used to make admixes at 0, 1.0, 2.5, 5, 10, 15, and 20% CA levels to build a standard curve using a viscometric assay. To make 75 g of each admix, appropriate aliquots of 100% CA flour was blended with N58-D1 commodity corn flour based on the dry weight of the flours. Alpha-amylase activity was determined by measuring the viscosity reduction activity of these Corn Amylase admixes on starch substrate. Viscosity was measured using a RVA-4 visco-analyzer (Newport Scientific). To set up the reactions, the moisture content of the starch substrate (Food grade from supermarkets) was first determined by using the method described above. A viscometer vessel was then placed on a scale and the scale was calibrated to zero. 2.7 g dry weight of starch was added into the viscometer vessel. 0.3 g dry weight of each of the CA admixes was weighed on a separate analytical balance and then added to the viscometer vessel. 50 mM sodium acetate, pH 5 buffer was then added to the vessel to bring the total contents of the vessel to 30.00 g. The content of the vessel was then thoroughly mixed so that the mixture was homogenous and no clumps were present in the vessel. A viscometer paddle was then inserted inside the vessel and the vessel was placed inside a pre-warmed RVA-4 visco-analyzer quickly to start the analysis. Table 2 shows the analysis method used on the RVA-4.

TABLE 2

RVA-4 viscosity analysis parameters

| Time | Type of changes | Values |
|---|---|---|
| 00:00:00 | Temp | 50° C. |
| 00:00:00 | Speed | 960 rpm |
| 00:00:10 | Speed | 160 rpm |
| 00:01:00 | Temp | 50° C. |
| 00:06:00 | Temp | 90° C. |
| 00:08:00 | Temp | 90° C. |
| 00:10:00 | Temp | 50° C. |

Time between readings: 4 sec

The viscosity readings at 7.2 minutes were recorded for each admix in the standard curve set (0, 1.0, 2.5, 5.0, 10.0, 15.0, and 20.0% CA) in triplicate and analyzed using JMP software package (SAS Institute). The viscosity readings were log-transformed (base 10), and a least squares regression model was used to generate the standard curves and estimate slopes and y-intercepts. For all samples, graphs of the data indicated a linear relationship between viscosity and dose of corn amylase. The slopes and y-intercepts were all significant ($p<0.001$) and were used to generate the following equation:

$$\text{Log}_{10}(\text{Viscosity}) = y\text{-intercept} - \text{slope} * (\text{Dose})$$

Measuring Viscosity of Bag Blend Samples:

Viscosity of the flour from harvested bag blends of 5% and 15% CA was measured in triplicate using the same method. The standard curve described above indicated that viscosity plotted against the admix ratio was linear from 0% CA to 20% CA. No activity was detected in the negative control.

For flour from harvested bag blends of 25% CA, the samples were first diluted by mixing them with equal amounts of commodity corn N58-D1 flour to reach the CA level of approximately 12.5% in order to stay within the linear range of the standard curve. Viscosity of the samples was then measured on RVA-4 in triplicate. Corn Amylase admix ratio in the grain was then calculated using the standard curves based on the following formula:

Dose of CA(%)=($\log_{10}$(Avg Observed Viscosity)-$Y$-Intercept)/Slope

Harvested bag blend samples were collected from each location as described under the heading "Samples for Corn Amylase bag blend." The predicted admix level for each hybrid at each location was determined as described above. There was considerable variation from the predicted admix levels when comparing the same hybrid across several locations. In addition, there was considerable variation between hybrids when hybrids at the same location were compared. Data for all of the hybrids at all of the locations were combined together and demonstrate that admix level can be predicted based upon the technique described above for producing the bag blend and is shown in Table 3.

TABLE 3

Corn Amylase grain admix levels measured using viscometric assay

| Seed CA Admix (%) | Grain CA Admix (%) |
|---|---|
| 5 | 8.1 |
| 15 | 18.7 |
| 25 | 28.2 |

Example 13

Samples for *Thermomyces lanuginosus* Glucoamylase and Corn Amylase Bag Blend

Seeds from a homogeneous, hemizygous *Thermomyces lanuginosus* glucoamylase (TlGA) expressing corn hybrid and a homogeneous, hemizygous Corn Amylase (CA) expressing corn hybrid were blended at the ratio of 80% TlGA:20% CA to constitute the control entry. These blended seeds were further blended with isogenic negative corn hybrid seeds which formed the bag blend test entry at the ratio of 90% Negative:10% (80% TlGA:20% CA). Both control and test entry were planted in one geographic location. The control entry (80% TlGA:20% CA) was self-pollinated. All ears from the control entry were harvested by rows (20 rows total) to generate 20 samples. Grain aliquots of 150 g were taken from each sample and 10 random samples were mixed to make two composite samples (Batch 1 and Batch 2). The test entry (90%/Negative:10% (80% TlGA:20% CA)) was planted as a single unit containing 32 rows wide and 6 blocks of 15 foot rows, and was allowed to open pollinate to simulate natural mixing of transgenic and nontransgenic pollen. The center rows (15 rows total) of the center block of the test entry were harvested to generate 15 samples. From the grain produced in the test entry, 150 g aliquots were taken from each sample and 7 and 8 random samples were mixed to make two composite samples (Batch 1 and Batch 2). All four composite samples and commodity corn NK N58-D1 were milled using a Perten Laboratory 3600 Disc Mill at setting 0. Flour moisture content was taken by using approximately 0.75 g of flour on the Mettler Toledo HB43 Halogen Moisture Analyzer at 130° C. The moisture content was used to calculate dry weight using the formula:

(Wet weight)=(dry weight)/(1-(% flour moisture/100))

Standard Curve for Predicting CA Admix Ratio:

Flour from control corn (80% TlGA:20% CA) was used to make admixes at 0, 1.0, 2.5, 5, 10, 15, and 20% CA levels to build a standard curve using a viscometric assay. To make 75 g of each admix, appropriate aliquots of control corn flour was blended with N58-D1 commodity corn flour based on the dry weight of the flours. Alpha-amylase activity was determined by measuring the viscosity reduction activity of these Corn Amylase admixes on starch substrate. It should be noted that TlGA in the flours would be inactivated during the viscosity assay and hence had no impact on viscosity reduction of starch substrate (Experimental data not shown). Viscosity was measured using a RVA-4 visco-analyzer (Newport Scientific). To set up the reactions, moisture content of the starch substrate (Food grade from supermarkets) was first determined by using the method described above. A viscometer vessel was then placed on a scale and the scale was calibrated to zero. 2.7 g dry weight of starch was added into the viscometer vessel. 0.3 g dry weight of each of the CA admixes was weighed on a separate analytical balance and then added to the viscometer vessel. 50 mM sodium acetate, pH 5 buffer was then added to the vessel to bring the total contents of the vessel to 30.00 g. The content of the vessel was then thoroughly mixed so that the mixture was homogenous and no clumps were present in the vessel. A viscometer paddle was then inserted inside the vessel and the vessel was placed inside a pre-warmed RVA-4 visco-analyzer quickly to start the analysis. The analysis method used on the RVA-4 is shown in Table 2 above.

The viscosity readings at 7.2 minutes were recorded for each admix in the standard curve set (0, 1.0, 2.5, 5.0, 10.0, 15.0, and 20.0% CA) in triplicate and analyzed using JMP software package (SAS Institute). The viscosity readings were log-transformed (base 10), and a least squares regression was used to generate the standard curves and estimate slopes and y-intercepts. For both control samples (Batch 1 and Batch 2), graphs of the data indicated a linear relationship between viscosity and dose of corn amylase. The slopes and y-intercepts were all significant ($p<0.001$) and were used to generate the following equation:

$\log_{10}$(Viscosity)=$y$-intercept-slope*(Dose)

The standard curve described above indicated that viscosity plotted against the admix ratio was linear from 0% CA to 20% CA. No activity was detected in the negative control.

Measuring CA Admix Ratios of Bag Blend Samples:

Viscosity of the two batches of flours from the harvested test corn (90%/Negative:10% (80% TlGA:20% CA)) was measured in triplicate using the same method. Corn Amylase admix ratio in the test corn was then calculated using the standard curves based on the following formula:

Dose of CA(%)=($\log_{10}$(Avg Observed Viscosity)-$Y$-Intercept)/Slope

Results shown in Table 4 demonstrated that CA admix level can be predicted based upon the technique described above for producing the bag blend. The percentage in column 4 is representative of the total transgenic enzyme in the blend (CA and TIGA).

TABLE 4

Corn Amylase grain admix levels measured using viscometric assay

| Seed admix | Batch | Grain CA admix (%) | Average grain CA admix (%) |
|---|---|---|---|
| 90% Negative:10% (80% TIGA:20% CA) | 1 | 7.6 | 8.2 |
| 90% Negative:10% (80% TIGA:20% CA) | 2 | 8.7 | |

Measuring TIGA Admix Ratios of Bag Blend Samples:

Harvested bag blend samples were collected and prepared as described under the heading "Samples for *Thermomyces lanuginosus* glucoamylase and Corn Amylase bag blend". Approximately 3 g of each of the flour samples (control corn and test corn) in triplicate were weighed into 50 ml conical centrifuge tubes. 40 ml of 1 mM EDTA solution was added to each tube. A Rotator was then used to mix the tubes by inversion for one hour at room temperature. The tubes were then centrifuged at 1500×g for 15 min at 4° C. A portion of supernatant which was termed an extract was then removed for assay.

Glucoamylase activity in corn flour was determined by measuring the amount of glucose produced in one hour from soluble starch substrate at pH 5.5 and 50° C. The assay buffer was pH 5.5 McIlvanes buffer modified by addition of EDTA to a final concentration of 1 mM. The EDTA was included in the extraction and the assay buffer to inhibit any α-amylase that was extracted and thus prevent it from interfering with the assay. The substrate is 2% (w/v) soluble starch in 1 mM EDTA.

Extracts were diluted serially in assay buffer prior to assay. The dilutions were 3.5-fold, 12.25-fold & 42.88-fold. Each extract was assayed in triplicate.

Substrate was aliquoted (50 μl/well) into two 96-well PCR plates that were kept on ice. Diluted extract (50 μl/well) was then added and mixed into the substrate. The plates were sealed then transferred to pre-cooled thermocyclers. One plate (the 0 min plate) was heated from 1° C. to 95° C. at the maximum rate (approximately 1 min was required), held at 95° C. for 10 min then cooled to 1° C. at the maximum rate. TIGA rapidly loses activity above 70° C., thus the 95° C. step inactivates the enzyme and stops the reaction. The other plate (the 60 min plate) was heated from 1° C. to 50° C. at the maximum rate and held at 50° C. for 60 min. The reaction was stopped by stepping the temperature to 95° C. and held at 95° C. for 10 min then cooled to 1° C. at the maximum rate.

Glucose generated in the above reactions was determined by using glucose assay reagent purchased from Megazyme (Catalog #: K-Gluc) and prepared following vendor's instructions. 10 μl of the content from each well of the two TIGA reaction PCR plates described above was transferred to fresh 96-well microtiter plates. Glucose standards (0 to 2 mg/ml) were also pipetted (10 μl/well) in duplicate into the fresh plates to generate a glucose standard curve. Glucose assay reagent (200 μl/well) was added with mixing. The microtiter plates were incubated at 40° C. for 20 min and absorbance at 510 nm was then measured. The glucose content of the reactions was determined by reference to the standard curve. The activity of the negative control was negligible.

One unit of GA activity was defined as the amount of enzyme that produced 1 μmol of glucose per min in the assay. Results from assays that fell within the linear range of the assay (0.5-10 mU per assay) were averaged.

Results shown in Table 5 demonstrated that TIGA admix level in the trial can be predicted based upon the technique described above for producing the bag blend. The percentage in column 5 is representative of the total transgenic enzyme in the blend (CA and TIGA).

TABLE 5

TIGA grain admix levels measured using colorimetric glucose assay

| Seed admix | Batch | Average grain TIGA activity (U/g) | Average activity among batches (U/g) | Average grain TIGA admix (%) |
|---|---|---|---|---|
| 80% TIGA:20% CA | 1 | 29.0 | 32.4 | 100 |
| 80% TIGA:20% CA | 2 | 35.8 | | |
| 90% Negative:10% (80% TIGA:20% CA) | 1 | 2.4 | 2.2 | 6.7 |
| 90% Negative:10% (80% TIGA:20% CA) | 2 | 2.0 | | |

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method to produce a predetermined level of a transgenic trait in a harvested crop comprising:
    a) measuring expression level of the transgenic trait in a first variety of seeds;
    b) determining the yield potential of said first variety of seeds;
    c) determining the yield potential of a second variety of seeds;
    d) calculating a blend ratio of the first variety of seeds to the second variety of seeds that will produce the predetermined level of the transgenic trait in the harvested crop, wherein the predetermined level of the trait in the harvested crop, the expression level of a trait in the first variety of seeds, yield potential of said first variety of seeds and the yield potential of said second variety of seeds are used to determine the blend ratio of the first variety of seeds to the second variety of seeds; wherein the calculating is performed using the equation $E(A)=(X_A \times Z_A \times Y_A)/[(Z_A \times Y_A)+(Z_O \times Y_O)]$; wherein $E(A)$ is the amylase activity in the harvested grain, $X_A$ is the expression level of amylase in grain, $Y_A$ is the yield potential of the amylase expressing corn variety, $Z_A$ is the percentage of trait expressing corn variety, $Y_O$ is the yield potential of the non-trait corn variety, and $Z_O$ is the percentage of non-trait corn variety; and wherein $E(A)$ is in activity units per mass unit, X is in activity units per mass unit, Y is in weight units per surface unit and the Z percentages are determined by weighing both varieties prior to seed blending;
    e) blending the first variety of seeds with the second variety of seeds to the blend ratio calculated in step d);

f) planting the blend of seeds; and g) harvesting the crop with the predetermined level of the transgenic trait, wherein said transgenic trait of interest is an enzyme, wherein said enzyme is an amylase.

2. The method of claim 1, wherein the seeds from each variety are blended prior to distribution to a seed grower.

3. The method of claim 1, wherein said blending occurs at the time of planting said seeds.

4. The method of claim 1, wherein the percentage of the variety of seed that will produce said transgenic trait is between 0.1% and 99.9% of the total blend.

5. The method of claim 1, wherein said first variety of seed is distinguishable from said second variety of seed.

6. The method of claim 5, wherein said first variety of seed is distinguishable from said second variety of seed by having a distinct seed coat color.

7. The method of claim 5, wherein said first variety of seed is distinguishable from said second variety of seed by having a distinct seed treatment.

8. The method of claim 1, wherein said crop is obtained from a plant selected from the group consisting of rice, barley, potato, sweet potato, canola, sunflower, rye, oats, wheat, corn, soybean, sugar beet, tobacco, *Miscanthus* grass, Switch grass, safflower, cotton, cassava, tomato, sorghum, alfalfa and sugarcane.

* * * * *